US011751841B2

(12) United States Patent
Gallippi et al.

(10) Patent No.: US 11,751,841 B2
(45) Date of Patent: Sep. 12, 2023

(54) METHODS, SYSTEMS, AND COMPUTER READABLE MEDIA FOR EVALUATING MECHANICAL ANISOTROPY FOR BREAST CANCER SCREENING AND MONITORING RESPONSE TO THERAPY

(71) Applicant: The University of North Carolina at Chapel Hill, Chapel Hill, NC (US)

(72) Inventors: Caterina Gallippi, Cary, NC (US); Gabriela Torres, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 17/176,772

(22) Filed: Feb. 16, 2021

(65) Prior Publication Data

US 2021/0259657 A1    Aug. 26, 2021

Related U.S. Application Data

(60) Provisional application No. 62/977,127, filed on Feb. 14, 2020.

(51) Int. Cl.
*A61B 8/08*  (2006.01)
*A61B 8/00*  (2006.01)

(52) U.S. Cl.
CPC ........... *A61B 8/0825* (2013.01); *A61B 8/485* (2013.01); *A61B 8/5207* (2013.01); *A61B 8/429* (2013.01)

(58) Field of Classification Search
CPC ..... A61B 8/0825; A61B 8/485; A61B 8/5207; A61B 8/329
See application file for complete search history.

(56) References Cited

U.S. PATENT DOCUMENTS

| 5,524,636 | A | * | 6/1996 | Sarvazyan | ............. | A61B 5/064 |
| | | | | | | 73/818 |
| 6,418,776 | B1 | | 7/2002 | Gitis et al. | | |

(Continued)

FOREIGN PATENT DOCUMENTS

SU      1392447 A      4/1988
WO   WO-2017197404 A1 *  11/2017  ............... A61B 5/00

OTHER PUBLICATIONS

Katrin Skerl et al., "Anisotropy of solid breast lesions in 2D shear wave elastography is an indicator of malignancy", 2016, University of Dundee (Year: 2016).*

(Continued)

*Primary Examiner* — Joel Lamprecht
*Assistant Examiner* — Brooke Lyn Klein
(74) *Attorney, Agent, or Firm* — Jenkins, Taylor & Hunt, P.A.

(57) ABSTRACT

A method for evaluating mechanical anisotropy of a material sample to determine a characteristic of the sample includes interrogating a material sample a plurality of times. Each interrogation includes: applying a force having a direction, having a coronal plane normal to the direction of the force, and having an oval or other profile with long and short axes within the coronal plane, the long axis being oriented at a specified angle from a reference direction within the coronal plane; and measuring displacement of the material sample resulting from application of the force. The interrogations are taken at different angles of orientation within the coronal plane and different portions of the material sample are interrogated. For each measurement one or more parameters are calculated for the respective angle of orientation. A degree of anisotropy of the one or more parameters is determined and used to evaluate a characteristic of the material sample.

8 Claims, 13 Drawing Sheets

(56) References Cited

U.S. PATENT DOCUMENTS

| | | | |
|---|---|---|---|
| 7,497,134 | B2 | 3/2009 | Renken et al. |
| 7,535,217 | B2 | 5/2009 | Quandt et al. |
| 8,734,351 | B2* | 5/2014 | Waki .................... A61B 8/463 |
| | | | 600/442 |
| 8,753,277 | B2 | 6/2014 | McAleavey |
| 9,211,111 | B2 | 12/2015 | Tamura |
| 9,244,041 | B2 | 1/2016 | Gallippi et al. |
| 10,772,608 | B2 | 9/2020 | Kanayama |
| 11,397,227 | B2 | 7/2022 | Gallippi et al. |
| 11,445,914 | B2 | 9/2022 | Gallippi et al. |
| 2003/0182069 | A1 | 9/2003 | Banes et al. |
| 2007/0088210 | A1 | 4/2007 | Woo et al. |
| 2011/0287948 | A1 | 11/2011 | Suresh et al. |
| 2013/0046175 | A1 | 2/2013 | Sumi |
| 2013/0181722 | A1 | 7/2013 | Pfaff |
| 2014/0046187 | A1 | 2/2014 | Taniguchi et al. |
| 2015/0320394 | A1 | 11/2015 | Arnal et al. |
| 2015/0362564 | A1 | 12/2015 | Wan et al. |
| 2018/0014814 | A1* | 1/2018 | Labyed .................. A61B 8/485 |
| 2018/0296191 | A1* | 10/2018 | Mellema .............. A61B 8/5276 |
| 2019/0183344 | A1 | 6/2019 | Gallippi et al. |
| 2021/0239775 | A1 | 8/2021 | Gallippi et al. |
| 2021/0293677 | A1 | 9/2021 | Gallippi et al. |

OTHER PUBLICATIONS

Alireza Nabavizadeh, "Viscoelastic biomarker for differentiation of benign and malignant breast lesion in ultra-low frequency range", 2019, Nature.com (Year: 2019).*

Non-Final Office Action for U.S. Appl. No. 16/301,085 (dated Sep. 24, 2021).

Commonly-Assigned, Co-pending U.S. Appl. No. 17/204,919 for "Quantitative Viscoelastic Response (QVISR) Ultrasound," (Unpublished, filed Mar. 17, 2021).

Hossain et al., "Improvement in Inclusion Contrast-to-Noise Ratio for Low-Displacement Acoustic Radiation Force (ARF) Elasticity Imaging Using a 3D Kernel Blind-Source Separation (BSS) Based Displacement Estimator," 2019 IEEE International Ultrasonics Symposium (IUS), pp. 1395-1398 (Oct. 2019).

Yokoyama et al., "Double-profile intersection (DoPIo) elastography: a new approach to quantifying tissue elasticity," 2019 IEEE International Ultrasonics Symposium (IUS), pp. 1-4 (Oct. 2019).

Hossain et al., "Evaluating Renal Transplant Status Using Viscoelastic Response (VISR) Ultrasound," Ultrasound in Med. & Biol., vol. 44, No. 8, pp. 1573-1584 (2018).

Moore et al., "In Vivo Viscoelastic Response (VisR) Ultrasound for Characterizing Mechanical Anisotrophy in Lower-Limb Skeletal Muscles of Boys with and without Duchenne Muscular Dystrophy," Ultrasound in Med Biol., vol. 44, No. 12, pp. 1-23 (Dec. 2018).

Hossain et al., "Acoustic Radiation Force Impulse-Induced Peak Displacements Reflect Degree of Anisotrophy in Transversely Isotropic Elastic Materials," IEEE Transactions on Ultrasonics, Ferroelectrics, and Frequency Control, vol. 64, No. 6, pp. 989-1001 (Jun. 2017).

Barr et al., "WFUMB Guidelines and Recommendations for Clinical Use of Ultrasound Elastography: Part 2: Breast," Ultrasound in Med. & Biol., vol. 41, No. 5, pp. 1148-1160 (2015).

Shiina et al., "WFUMB Guidelines and Recommendations for Clinical Use of Ultrasound Elastogrpahy: Part 1: Basic Principles and Terminology," Ultrasound in Med. & Biol., vol. 41, No. 5, pp. 1126-1147 (2015).

Ferraioli et al., "WFUMB Guidelines and Recommendations for Clinical Use of Ultrasound Elastography: Part 3: Liver," Ultrasound in Med & Biol., vol. 41, No. 5, pp. 1161-1179 (2015).

Czernuszewicz et al., "Experimental Validation of Displacement Underestimation in ARFI Ultrasound," Ultrason Imaging, vol. 35, No. 3, pp. 1-24 (Jul. 2013).

Dhanaliwala et al, "Assessing and improving acoustic radiation force image quality using a 1.5D transducer design," IEEE Trans Ultrason Ferroelectr Freq Control, vol. 59, No. 7, pp. 1-16 (Jul. 2012).

Nightingale, "Acoustic Radiation Force Impulse (ARFI) Imaging: a Review," Curr Med Imaging Rev., vol. 7, No. 4, pp. 1-24 (Nov. 1, 2011).

Pedregosa et al., "Scikit-learn: Machine Learning in Python," Journal of Medicine Learning Research, arXiv:1201.0490v4, vol. 12, pp. 1-6 (2011).

Ostrovsky et al., "Radiation force and shear motions in inhomogeneous media," The Journal of Acoustical Society of America, vol. 121, No. 1324 pp. 1-9 (2007).

Palmeri et al., "Ultrasonic Tracking of Acoustic Radiation Force-Induced Displacements in Homogeneous Media," IEEE Trans Ultrason Ferroelectr Freq Control, vol. 53, No. 7, pp. 1-24 (Jul. 2006).

Jensen et al., "Simulation of advanced ultrasound systems using Field II," In IEEE International Symposium on Biomedical Engineering, pp. 1-5 (2004).

Chen et al., "Quantifying elasticity and viscosity from measurement of shear wave speed dispersion," J. Acoust. Soc. Am., vol. 115, No. 6, pp. 2781-2785 (Jun. 2004).

Nightingale et al., "Sheav-wave Generation Using Acoustic Radiation Force: In Vivo and Ex Vivo Results," Ultrasound in Med. & Biol., vol. 29, No. 12, pp. 1-9 (2003).

Sandrin et al., "Transient Elastography: A New Noninvasive Method for Assessment of Hepatic Fibrosis," Ultrasound in Med. & Biol., vol. 29, No. 12, pp. 1-9 (2003).

McAleavey et al., "Estimates of Echo Correlation and Measurement Bias in Acoustic Radiation Force Impulse Imaging," IEEE Transactions on Ultrasonics, Ferroelectrics, and Frequency Control, vol. 50, No. 6, pp. 631-641 (Jun. 2003).

Nightingale et al., "Acoustic Radiation Force Impulse Imaging: In Vivo Demonstration of Clinical Feasibility," Ultrasound in Medicine and Biology, pp. 1-21 (Oct. 24, 2001).

Chan et al., "Active Contours Without Edges," IEEE Transactions on Image Processing, vol. 10, No. 2, pp. 266-277 (Feb. 2001).

Torr, "MLESAC: A New Robust Estimator with Application to Estimating Image Geometry," Computer Vision and Image Understanding, vol. 78, pp. 138-156 (2000).

Sarvazyan et al., "Shear Wave Elasticity Imaging: A New Ultrasonic Technology of Medical Diagnostics," Ultrasound in Med. & Biol., vol. 24, No. 9, pp. 1419-1435 (1998).

Walker et al., "A Fundamental Limit on Delay Estimation Using Partially Correlated Speckle Signals," IEEE Transactions on Ultrasonics, Ferroelectrics, and Frequency Control., vol. 42, No. 2, pp. 301-308 (Mar. 1995).

Ponnekanti et al., "Fundamental Mechanical Limitations on the Visualization of Elasticity Contrast in Elastography," Ultrasound in Med. & Biol., vol. 21, No. 4, pp. 533-543 (1995).

Jensen et al., "Calculation of Pressure Fields from Arbitrarily Shaped, Apodized, and Excited Ultrasound Transducers," IEEE Transactions on Ultrasonics, Ferroelectrics, and Frequency Control, vol. 39, No. 2, pp. 1-7 (1992).

Smith et al., "Properties of Acoustical Speckle in the Presence of Phase Aberration Part II: Correlation Lengths," Ultrasonic Imaging, pp. 29-51 (1988).

Trahey et al., "Properties of Acoustical Speckle in the Presence of Phase Aberration Part I: First Order Statistics," Ultrasonic Imaging, pp. 12-28 (1988).

Wagner et al., "Statistics of Speckle in Ultrasound B-Scans," IEEE Transactions on Sonics and Ultrasonics, vol. 30, No. 3, pp. 156-163 (May 1983).

Fritsch et al., "Monotone Piecewise Cubic Interpolation," Siam J. Numer. Anal., vol. 17, No. 2, pp. 238-246 (Apr. 1980).

Graustein, "Homogeneous Cartesian Coordinates, Linear Dependence of Points and Lines," Introduction to Higher Geometry, Chapter III, pp. 1-22 (1930).

Commonly-Assigned, Co-pending U.S. Appl. No. 17/150,612 for "Methods, Systems, and Computer-Readable Media for Nondestructively Quantitatively Measuring Physical Properties of a Material by Observing Induced Displacements Using Different Focal Configurations," (Unpublished, filed Jan. 15, 2021).

Hossain et al., "Viscoelectric Response Ultrasound Derived Relative Elasticity and Relative Viscosity Reflect True Elasticity and Viscosity: In Silico and Experimental Demonstration," IEEE Trans-

(56) References Cited

OTHER PUBLICATIONS actions on Ultrasonics, Ferroelectrics, and Frequency Control, vol. 67, No. 6, pp. 1102-1117 (Jun. 2020).
Zhang et al., "Fluidity and elasticity form a concise set of viscoelastic biomarkers for breast cancer diagnosis based on Kelvin-Voigt fractional derivative modeling," Springer, pp. 1-16 (Apr. 25, 2020).
Torres et al., "Viscoelastic Response (VisR)-Derived Mechanical Anisotropy for Differentiating Malignant from Benign Breast Lesions in Women, in vivo," 2019 IEEE International Ultrasonic Symposium (IUS), pp. 1-3 (2019).
You et al., "Quantitative and Qualitative Evaluation of Breast Cancer Prognosis: A Sonographic Elastography Study," Med Sci Monit, vol. 25, pp. 1-8 (2019).
Sood et al., "Ultrasound for Breast Cancer Detection Globally: A Systematic Review and MetaAnalysis," Journal of Global Oncology, pp. 1-17 (Aug. 27, 2019).
Nabavizadeh et al., "Viscoelastic biomarker for differentiation of benign and malignant breast lesion in ultra-low frequency range," Scientific Reports, vol. 9, No. 5737, pp. 1-12 (2019).
Notification Concerning Transmittal of International Preliminary Report on Patentability for International Application Serial No. PCT/US2017/032745 (dated Nov. 22, 2018).
Chen et al., "Ultrasound shear wave elastography of breast lesions: correlation of anisotropy with clinical and histopathological findings," Cancer Imaging, vol. 18, No. 11, pp. 1-11 (2018).
Zahran et al., "Ultrasound elastography: How can it help in differentiating breast lesions?" The Egyptian Journal of Radiology and Nuclear Medicine, vol. 49, pp. 1-10 (2018).
Youk et al., "Shear-wave elastography in breast ultrasonography: the state of the art," Ultrasonography, vol. 36, No. 4, pp. 300-309 (Oct. 2017).
Notification of Transmittal of the International Search Report and the Written Opinion of the International Searching Authority, or the Declaration for International Application Serial No. PCT/US2017/032745 (dated Aug. 2017).
Selzo et al., "On the Quantitative Potential of Viscoelastic Response (VisR) Ultrasound Using the One-Dimensional Mass-Spring-Damper Model," IEEE Trans Ultrason Ferroelectr Freq Control, vol. 63, No. 9, pp. 1-29 (Sep. 2016).
Skerl et al., "Anisotropy of solid breast lesions in 2D shear wave elastography is an indicator of malignancy," Academic Radiology, vol. 23, No. 1, pp. 1-32 (2016).
Giannotti et al., "Shear-wave elastography and greyscale assessment of palpable probably benign masses: is biopsy always required?" Br J Radiol, vol. 89, pp. 1-7 (2016).
Kuzmiak, "Breast Cancer Survivors: Does the Screening MRI Debate Continue?" Acad Radiol, vol. 22, pp. 1329-1330 (2015).
Barr et al., "Shear-Wave Elastography of the Breast: Value of a Quality Measure and Comparison with Strain Elastography," Radiology, vol. 000, No. 0, pp. 1-9 (2015).
Grajo et al., "Strain Elastography for Prediction of Breast Cancer Tumor Grades," J Ultrasound Med, vol. 33, pp. 129-134 (2014).
Selzo et al., "Viscoelastic Response (VisR) Imaging for Assessment of Viscoelasticity in Voigt Materials," IEEE Trans Ultrason Ferroelectr Freq Control, vol. 60, No. 12, pp. 1-23 (Dec. 2013).
Rouze et al., "Finite Element Modeling of Impulsive Excitation and Shear Wave Propagation in an Incompressible, Traversely Isotropic Medium," J Biomech, vol. 46, No. 16, pp. 1-18 (Nov. 15, 2013).
Wang et al., "Imaging Transverse Isotropic Properties of Muscle by Monitoring Acoustic Radiation Force Induced Shear Waves Using a 2-D Matrix Ultrasound Array," IEEE Transactions on Medical Imaging, vol. 32, No. 9, pp. 1671-1684 (Sep. 2013).
Cole et al., "Assessing the Standalone Sensitivity of Computer-aided Detection (CADe) with Cancer Cases from the Digital Mammographic Imaging Screening Trial (DMIST)," AJR Am J Roentgenol., vol. 199, No. 3, pp. 1-20 (2012).
Berg et al., "Detection of Breast Cancer with Addition of Annual Screening Ultrasound or a Single Screening MRI to Mammography in Women with Elevated Breast Cancer Risk," JAMA, vol. 307, No. 13, pp. 1-18 (Apr. 4, 2012).
Qiu et al., "Ultrasonic Viscoelasticity Imaging of Nonpalpable Breast Tumors: Preliminary Results," Acad Radiol, vol. 15, No. 12, pp. 1-17 (Dec. 2008).
Pinton et al., "Rapid Tracking of Small Displacements with Ultrasound," IEEE Transactions on Ultrasonics, Ferroelectrics, and Frequency Control, vol. 53 No. 6, pp. 1103-1117 (Jun. 2006).
Palmeri et al., "A Finite-Element Method Model of Soft Tissue Response to Impulsive Acoustic Radiation Force," IEEE Transactions on Ultrasonics, Ferroelectrics, and Frequency Control, vol. 52, No. 10, pp. 1699-1712 (Oct. 2005).
Sinkus et al., "Imaging Anisotropic and Viscous Properties of Breast Tissue by Magnetic Resonance-Elastography," Magnetic Resonance in Medicine, vol. 53, pp. 372-387 (2005).
Notice of Allowance for U.S. Appl. No. 16/301,085 (dated May 11, 2022).
Notice of Allowance for U.S. Appl. No. 17/150,612 (dated Mar. 7, 2022).
Notice of Allowance for U.S. Appl. No. 16/301,085 (dated Jan. 28, 2022).

* cited by examiner

METHODS, SYSTEMS, AND COMPUTER READABLE MEDIA FOR EVALUATING MECHANICAL ANISOTROPY FOR BREAST CANCER SCREENING AND MONITORING RESPONSE TO THERAPY

PRIORITY CLAIM

This application claims the priority benefit of U.S. Provisional Patent Application No. 62/977,127, filed Feb. 14, 2020, the disclosure of which is incorporated herein by reference in its entirety.

GOVERNMENT INTEREST

This invention was made with government support under Grant Number HL092944 awarded by the National Institutes of Health. The government has certain rights in the invention.

BACKGROUND

Breast cancer screening is beneficial when it averts progression of disease to metastasis and/or death. However, adverse effects to patients (and unnecessary medical expense) may result downstream from false positives. The current imaging standard for differentiating malignant masses, digital mammography, has sensitivities ranging from 0.40 to 0.85. Combining Magnetic Resonance Imaging (MRI) with Brightness Mode (B-Mode) increases sensitivity but decreases specificity. Achieving early breast cancer detection with high sensitivity and specificity remains a challenge that may be met by exploiting radiation force ultrasound-based measures of the mechanical properties of tissue.

Thus, there is a need for improved methods for differentiating malignancy in breast cancer lesions and for monitoring response to neoadjuvant chemotherapy.

SUMMARY

The present disclosure demonstrates the feasibility of calculating viscoelastic anisotropy for differentiating malignancy in breast cancer lesions and for monitoring response to neoadjuvant chemotherapy.

Those skilled in the art will appreciate the scope of the present disclosure and realize additional aspects thereof after reading the following detailed description of the preferred embodiments in association with the accompanying drawing figures.

ABBREVIATIONS

At least some of the following abbreviations may be used in this disclosure. If there is an inconsistency between abbreviations, preference should be given to how it is used above. If listed multiple times below, the first listing should be preferred over any subsequent listing(s).
ARF Acoustic Radiation Force
ASIC Application Specific Integrated Circuit
B-Mode Brightness Mode
CPU Central Processing Unit
DoA Degree of Anisotropy
LDoA Lesion Degree of Anisotropy
SDoA Surrounding Tissue Degree of Anisotropy
DSP Digital Signal Processor
FPGA Field Programmable Gate Array
MRI Magnetic Resonance Imaging
PD Physical Displacement
RE Relative Elasticity
RV Relative Viscosity
SOC System on Chip
VisR Viscoelastic Response A method for evaluating mechanical anisotropy of a material sample to determine a characteristic of the sample includes interrogating a material sample a plurality of times, each interrogation comprising: applying a force having a direction, having a coronal plane normal to the direction of the force, and having an oval or other profile with long and short axes within the coronal plane, the long axis being oriented at a specified angle from a reference direction within the coronal plane; and measuring displacement of the material sample resulting from application of the force, wherein the interrogations are taken at different angles of orientation within the coronal plane and different portions of the material sample are interrogated. For each measurement one or more parameters are calculated for the respective angle of orientation. A degree of anisotropy is calculated for each of the parameters and used to evaluate a characteristic of the sample.

According to another aspect of the subject matter described herein, a system for evaluating mechanical anisotropy of a material sample to determine a characteristic of the sample is provided. The system includes an ultrasound transducer. The system further includes one or more processors. The system further includes memory storing instructions executable by the one or more processors for: controlling the ultrasound transducer to interrogate a material sample a plurality of times, each interrogation comprising: applying a force having a direction, having a coronal plane normal to the direction of the force, and having an oval or other profile with long and short axes within the coronal plane, the long axis being oriented at a specified angle from a reference direction within the coronal plane; and measuring displacement of the material sample resulting from application of the force, wherein the interrogations are taken at different angles of orientation within the coronal plane and different portions of the material sample are interrogated. The instructions stored in the memory are also executable by the one or more processors for, for each measurement, calculating one or more parameters for the respective angle of orientation; and determining and using a degree of anisotropy of the one or more parameters to evaluate a characteristic of the material sample.

According to another aspect of the subject matter described herein, a non-transitory computer readable medium having stored thereon executable instructions that when executed by a processor of a computer control the computer to perform steps is provided. The steps include controlling an ultrasound transducer to interrogate a material sample a plurality of times, each interrogation comprising: applying a force having a direction, having a coronal plane normal to the direction of the force, and having an oval or other profile with long and short axes within the coronal plane, the long axis being oriented at a specified angle from a reference direction within the coronal plane; and measuring displacement of the material sample resulting from application of the force, wherein the interrogations are taken at different angles of orientation within the coronal plane and different portions of the material sample are interrogated. The steps further include for each measurement, calculating one or more parameters for the respective angle of orientation. The steps further include determining and using a degree of anisotropy of the one or more parameters to evaluate a characteristic of the material sample.

The subject matter described herein can be implemented in software in combination with hardware and/or firmware. For example, the subject matter described herein can be implemented in software executed by a processor. In one exemplary implementation, the subject matter described herein can be implemented using a non-transitory computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The accompanying drawing figures incorporated in and forming a part of this specification illustrate several aspects of the subject matter described herein, and together with the description serve to explain the principles of the subject matter described herein.

DETAILED DESCRIPTION

Figure 1:
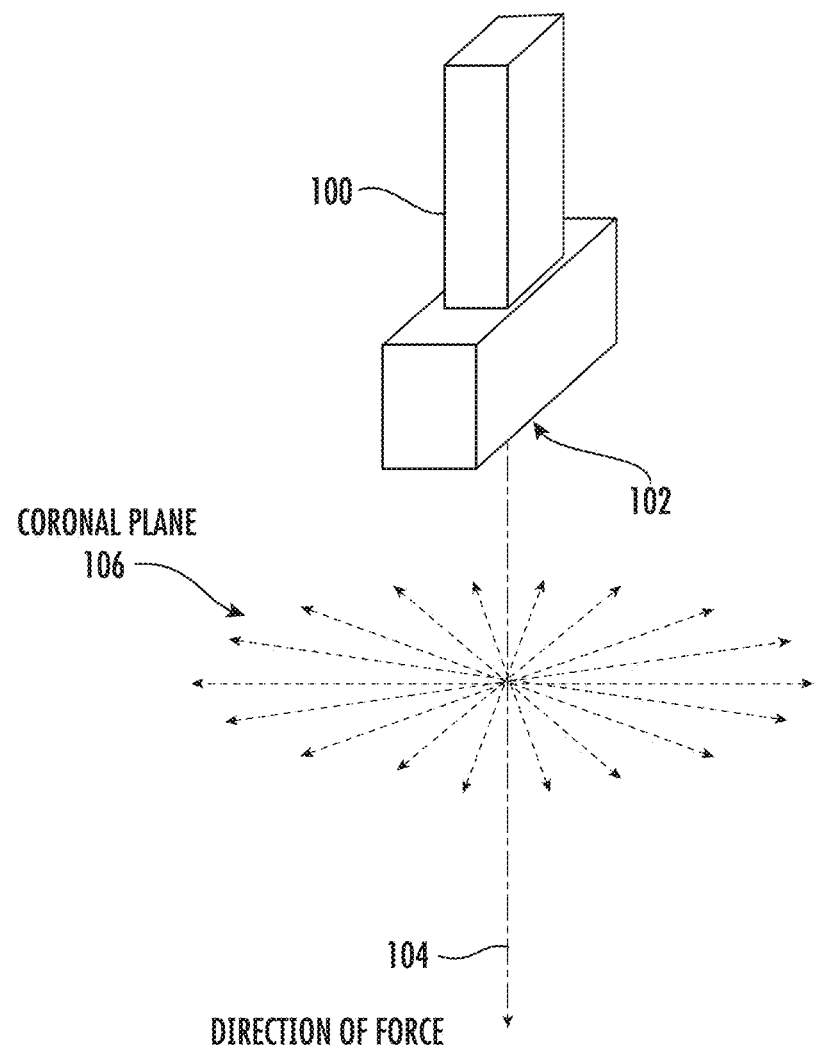
FIG. 1 illustrates an ultrasound transducer according to an embodiment of the subject matter described herein.

The technology presented herein utilizes Acoustic Radiation Force (ARF)-based ultrasound to excite tissue, and uses the resulting displacements and derived viscoelastic parameters to estimate the mechanical anisotropy of breast masses and their corresponding surrounding tissue to identify malignancy and monitor response to therapy. In one embodiment, the technique utilizes a standard ultrasound scanner with a linear ultrasound transducer to perform these measurements by taking the difference in each of the viscoelastic parameters between lesion and background, evaluated over 0, 30, 60, and 90 degrees of transducer rotation. Note that multi-dimensional or matrix array transducer could also be implemented, and that different angles or interrogation would also be relevant, including more or fewer interrogated angles. The difference between mass and background in mechanical anisotropy is relevant as a diagnostic metric for breast cancer, and it may also be relevant in other cancer applications.

In addition to measuring induced displacement, the ARF-based ultrasound imaging methods presented herein are also used to characterize the viscoelastic properties of tissue. Anisotropic tissues are those whose viscoelastic properties exhibit directional dependence, varying in amplitude and phase. The ability to image and quantify anisotropy may be diagnostically relevant to breast cancer because this pathology alters tissue structure and composition, and thereby the anisotropy of the lesion and its surrounding tissue. The present disclosure demonstrates techniques of calculating integrated viscoelastic anisotropy for differentiating malignancy in breast cancer lesions and for monitoring response to neoadjuvant chemotherapy.

The present disclosure presents the use of Viscoelastic Response (VisR) ultrasound-derived mechanical anisotropy measures, which have been demonstrated previously in humans in vivo for Duchenne muscular dystrophy and kidney transplants. ARF-based ultrasound imaging methods are used to characterize the viscoelastic properties of tissue. Anisotropic tissues are those whose viscoelastic properties exhibit directional dependence, varying in amplitude and phase. The ability to image and quantify anisotropy may be diagnostically relevant to breast cancer because this pathology alters tissue structure and composition, and thereby the anisotropy of the lesion and its surrounding tissue.

The embodiments set forth below represent the necessary information to enable those skilled in the art to practice the subject matter described herein and illustrate the best mode of practicing the subject matter described herein. Upon reading the following description in light of the accompanying drawing figures, those skilled in the art will understand the concepts of the subject matter described herein and will recognize applications of these concepts not particularly addressed herein. It should be understood that these concepts and applications fall within the scope of the disclosure and the accompanying claims.

FIG. 1 illustrates an ultrasound transducer according to an embodiment of the subject matter described herein. In the embodiment illustrated in FIG. 1, a transducer 100 includes an ultrasonic emitter array 102, which produces an Acoustic Radiation Force (ARF) having a direction of force 104. A coronal plane 106 is defined as the plane normal to the direction of force 104. In the embodiment illustrated in FIG. 1, the ultrasonic emitter array 102 comprises a linear array of emitter elements, and thus may alternatively be referred to as "linear array 102".

Figure 2:
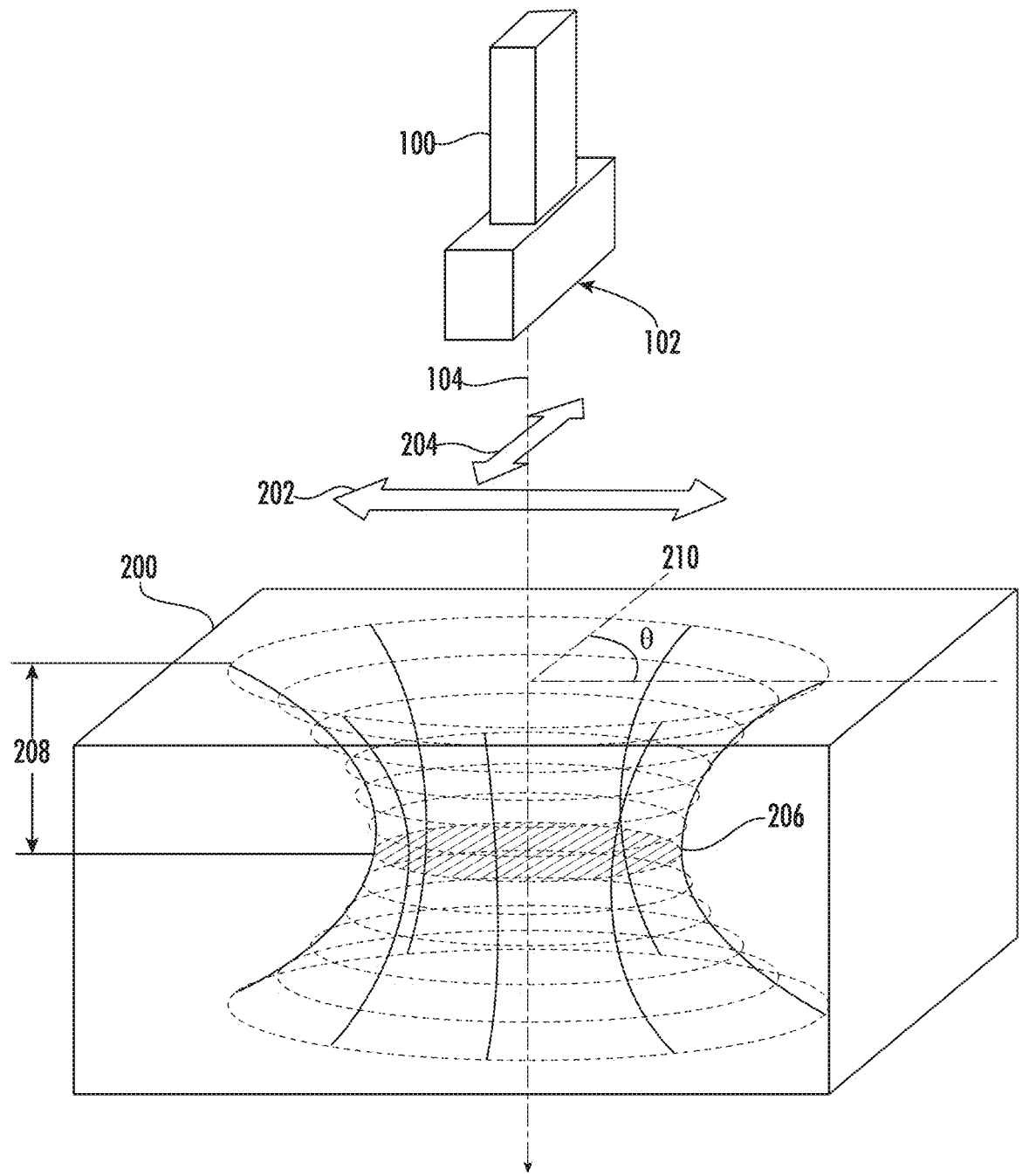
FIG. 2 illustrates the ultrasound transducer in use over a material sample, showing an oval force profile produced within the material sample.

FIG. 2 illustrates the ultrasound transducer in use over a material sample, showing an oval force profile produced within the material sample. In the embodiment illustrated in FIG. 2, the transducer 100 produces a force having a direction 104. The force is directed into a material sample 200, which may be tissue. In one mode of operation, the transducer 100 produces a force having an oval-shaped profile. In another mode of operation, the transducer produces a force having a circular or other profile with equi-length axes.

In the embodiment illustrated in FIG. 2, the transducer 100 is producing a force having an oval or other profile with a long axis 202 and a short axis 204. The shape delineated using dotted lines within the material sample 200 is intended to illustrate the point that the acoustic force produced by the transducer 100 has a point of highest energy 206—represented by a shaded oval—located at a focal depth 208 within the material 200. Above and below the focal depth 208, the size of the focal area expands and thus has a smaller energy per volume.

In the example illustrated in FIG. 2, the shape of the force profile at focal depth is an oval. The long axis of the oval force profile 202 has an angle theta ($\Theta$) relative to an arbitrarily chosen reference vector 210 associated with the material sample 200. For a transducer with a linear array of elements, the long axis of force 202 is perpendicular to the long axis of the array. To change the angle theta ($\Theta$), it is necessary to physically rotate the linear array 102 around an axis of rotation aligned with the direction of force 104. In another mode of operation (not shown in FIG. 2) the shape of the force profile at focal depth is circular.

Figure 3:
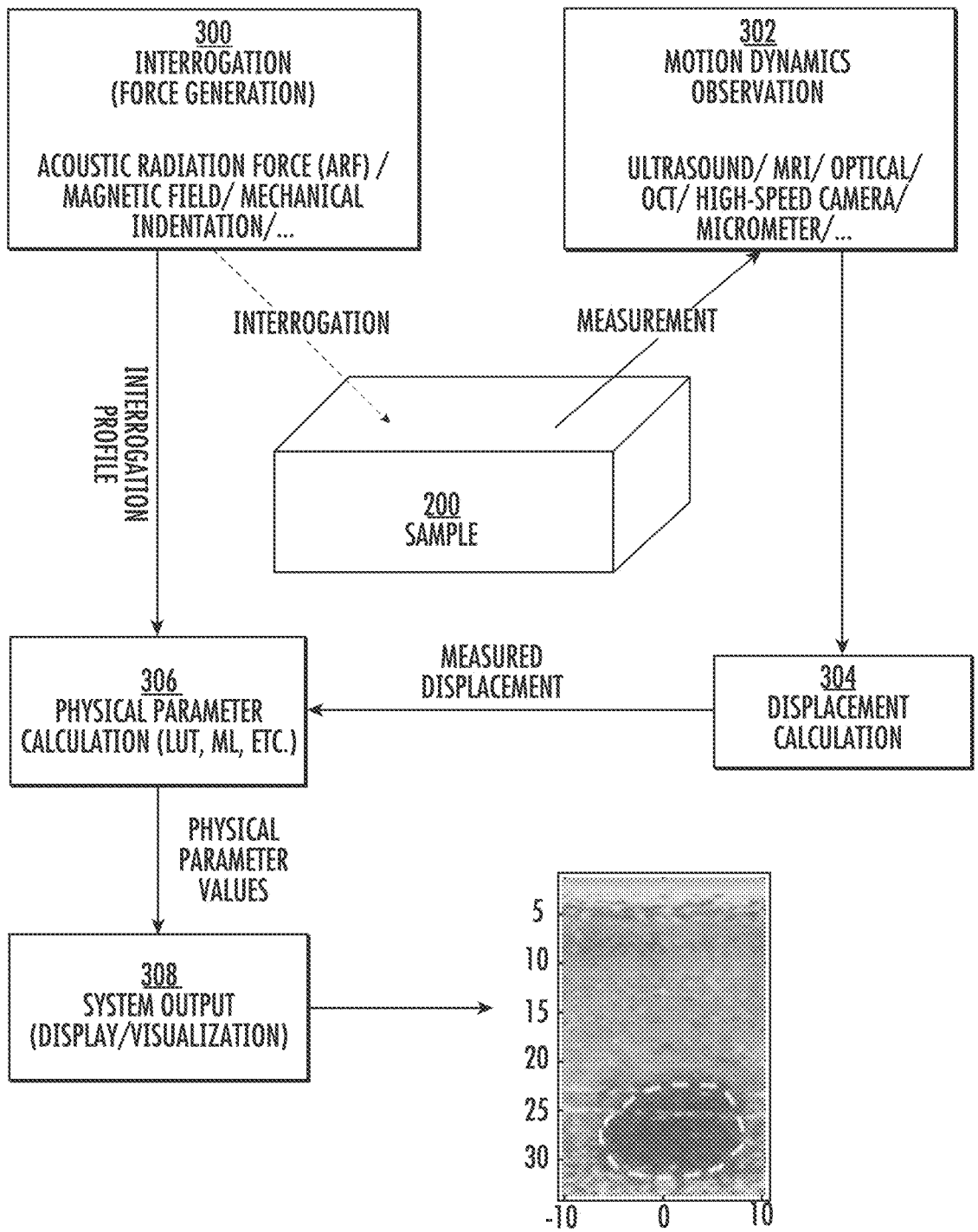
FIG. 3 is block diagram illustrating a system for evaluating mechanical anisotropy for breast cancer screening and monitoring response to therapy according to some embodiments of the subject matter described herein.

FIG. 3 is block diagram illustrating a system for evaluating mechanical anisotropy for breast cancer screening and monitoring response to therapy according to some embodiments of the subject matter described herein. In the embodiment illustrated in FIG. 3, the system includes a subsystem for interrogation (force generation) 300, a subsystem for motion dynamics observation 302, a subsystem for displacement calculation 304, a subsystem for physical parameter calculation 306, and a subsystem for producing system output 308.

The interrogation subsystem 300 may produce ARF, a mechanical indentation, and/or other means to cause a displacement within the material sample. In the embodiment illustrated in FIG. 3, the interrogation subsystem 300 produces a sequence of one or more forces directed towards a material sample according to an interrogation profile that defines an amount, direction, and/or focal depth of each force in the sequence of forces, as well as the timing, duration, spacing, relaxation time, recovery time, etc., of each force in the sequence of forces.

The motion dynamics observation subsystem 302 may make measurements based on ultrasound, magnetic resonance imagery, optical input (such as but not limited to pictures, videos, etc., including from high-speed cameras), optical coherence tomography, using a mechanical means, such as but not limited to a micrometer, and/or other means to observe the displacement caused by the interrogation of the sample. It should be noted that the angles of the forces and measurements with respect to the sample as shown in FIG. 3 were chosen for illustration purposes only and are not intended to convey any particular orientation.

The displacement calculation subsystem 304 receives data produced by the motion dynamics observation subsystem 302 and calculates displacement of the sample. In the embodiment illustrated in FIG. 3, the displacement calculation subsystem 304 receives data for each measurement. The physical parameter calculation subsystem 306 receives displacement information (e.g., the measured displacement) from the displacement calculation subsystem 304, as well as some or all of the interrogation profile received from the interrogation subsystem 300, and uses all or a portion of that information to calculate or derive a predicted value for one or more physical parameters.

The physical parameter calculation subsystem 306 produces as output values of the physical parameters of the material sample, such as the elasticity/viscosity of the material sample, which it provides to the system output subsystem 308. In the embodiment illustrated in FIG. 3, the system output subsystem 308 produces a "heat map" showing the values of the measured parameter at different locations (depth, lateral distance from centerline) of the measured sample.

Each of the systems, subsystems, or modules described herein may comprise processing circuitry. Processing circuitry may comprise a combination of one or more of a microprocessor, a controller, a microcontroller, a Central Processing Unit (CPU), a Digital Signal Processor (DSP), an Application Specific Integrated Circuit (ASIC), a Field Programmable Gate Array (FPGA), or any other suitable computing device, resource, or combination of hardware, software, and/or encoded logic operable to provide system functionality, either alone or in conjunction with other components, such as the device readable medium. For example, the processing circuitry may execute instructions stored in a device readable medium or in memory within and/or coupled to the processing circuitry. Such functionality may include providing any of the various features, functions, or benefits discussed herein. In some embodiments, the processing circuitry may include a System on a Chip (SOC).

Methods

Figure 4:
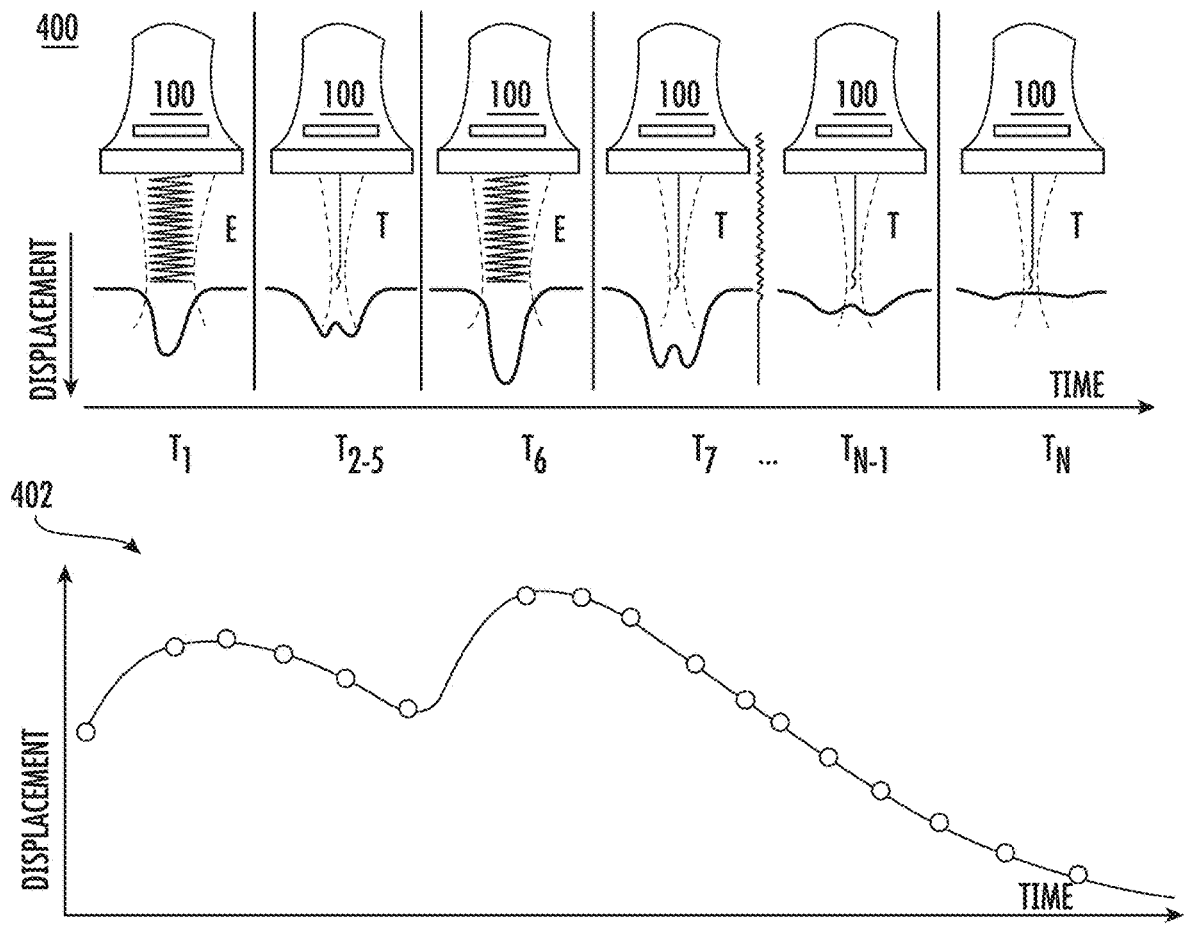
FIG. 4 illustrates an exemplary method for using Acoustic Radiation Force (ARF) to induce tissue displacements, and using the measured tissue displacements to estimate Relative Elasticity (RE) and Relative Viscosity (RV)

FIG. 4 illustrates an exemplary method for using ARF to induce tissue displacements, and using the measured tissue displacements to estimate Relative Elasticity (RE) and Relative Viscosity (RV). FIG. 4 shows an example sequence 400 of excitation pulses (E) and tracking pulses (T) generated by an ultrasound transducer 100. At time $T_1$, the transducer 100 generates an excitation pulse, then performs four tracking pulses, at times $T_2$ through $T_5$. At time $T_6$, the transducer 100 generates another excitation pulse, followed by N number of tracking pulses, at times $T_7$ through $T_N$. The resulting displacement is shown in graph 402. The curve is fitted to a model, e.g., using the equations shown in FIG. 4, and values of RE and RV can be derived from the measured displacement.

Figure 5:
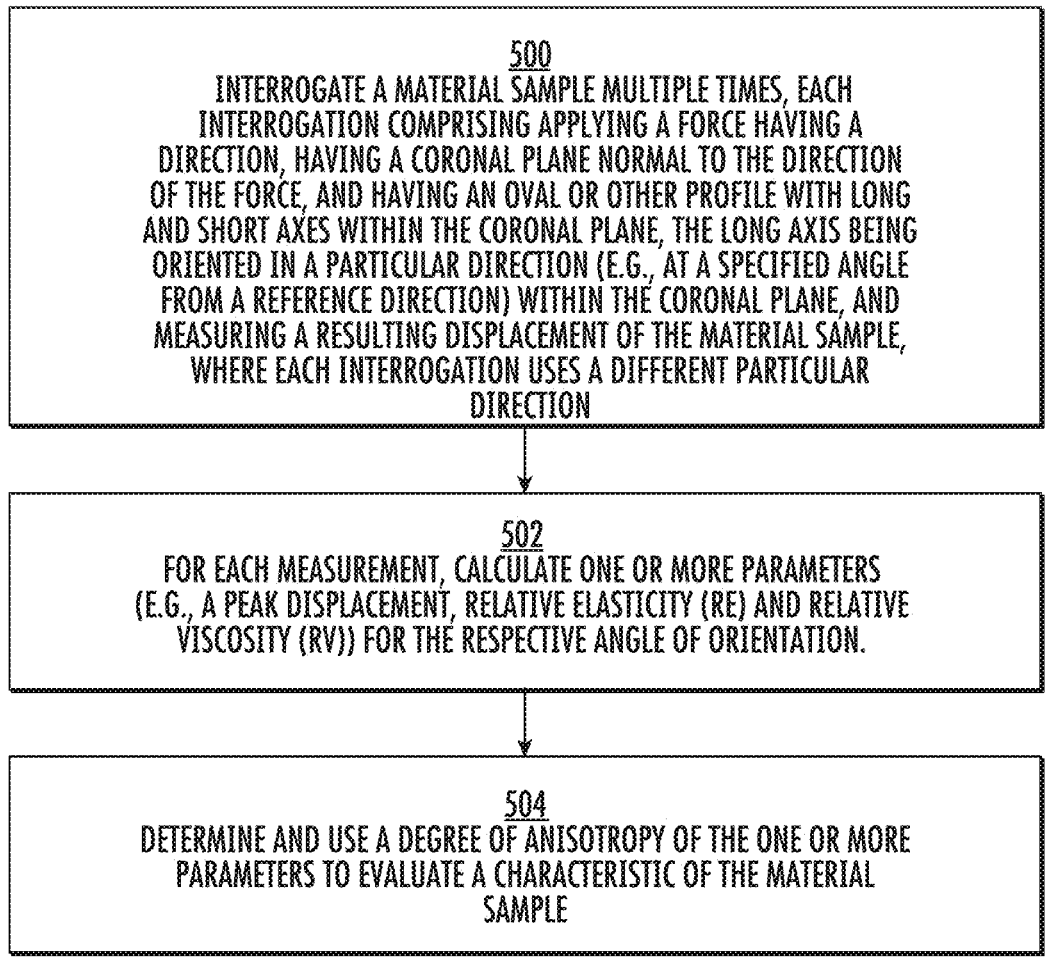
FIG. 5 illustrates an exemplary method for evaluating mechanical anisotropy for breast cancer screening and monitoring response to therapy according to some embodiments of the present disclosure.

FIG. 5 illustrates an exemplary method for evaluating mechanical anisotropy for breast cancer screening and monitoring response to therapy according to some embodiments of the present disclosure.

In step 500, a material sample (e.g., a breast tissue lesion in vivo) is interrogated multiple times, each interrogation involving applying a force having a direction, having a coronal plane normal to the direction of the force, and having an oval or other profile with long and short axes within the coronal plane, the long axis being oriented in a particular direction (e.g., at a specified angle from a reference direction) within the coronal plane, and measuring the resulting displacement of the material sample. The interrogations are taken at different orientations within the coronal plane (e.g., 0, 30, 60, and 90 degrees), and different portions of the material sample are interrogated (e.g., a breast tissue lesion and the surrounding tissue).

In step 502, for each measurement, one or more parameters (e.g., peak displacement, RE, RV, etc.) are calculated for the respective angle of orientation.

In step 504, a degree of anisotropy is determined for each of the one or more parameters, and the degree of anisotropy is used to evaluate a characteristic of the material sample. To determine the degree of anisotropy, the values calculated for each of the parameters are fit to a sinusoid (e.g., via a least-squares minimization) and extrapolated to 360 degrees to create at least one sinusoid representing a first portion of the material sample (e.g., a lesion) and another sinusoid representing a second portion of the material sample (e.g., the background). For each sinusoid, a degree of anisotropy of the respective parameter is determined based on the ratio of maximum to minimum values for that parameter. The sinusoids for a particular parameter are phase aligned.

From the phase-aligned sinusoids for each parameter, log(LDoA/SDoA) is calculated. Based on comparing results obtained from comparing log(LDoA/SDoA) of the different parameter values for known malignant versus benign masses, the log(LDoA/SDoA) for the different parameters can be calculated for tissue sample with a lesion that is not known to be malignant or benign and the results can be used to characterize the lesion as malignant or benign. For example: in one study, 30 breast lesions (9 malignant, 21 benign) were imaged in vivo in women with BIRADS-4 or -5 rating after standard screening. Lesions were sonographically visible with B-Mode ultrasound on diagnostic workup. Raw RF data were acquired using a Siemens S3000 Helix and a 9L4 ultrasonic transducer with a gyroscope to enable data acquisitions at 0°, 30°, 60°, and 90° orientations. VisR relative elasticity (RE), relative viscosity (RV), and peak displacement (PD) were measured for each transducer orientation, and fit to a sinusoid by least-squares minimization, extrapolating to 360°. Degree of Anisotropy (DoA) was evaluated as the ratio of the maximum to the minimum parameter value. For some patients, these in vivo results were compared to biopsy findings.

Results

Figure 6:
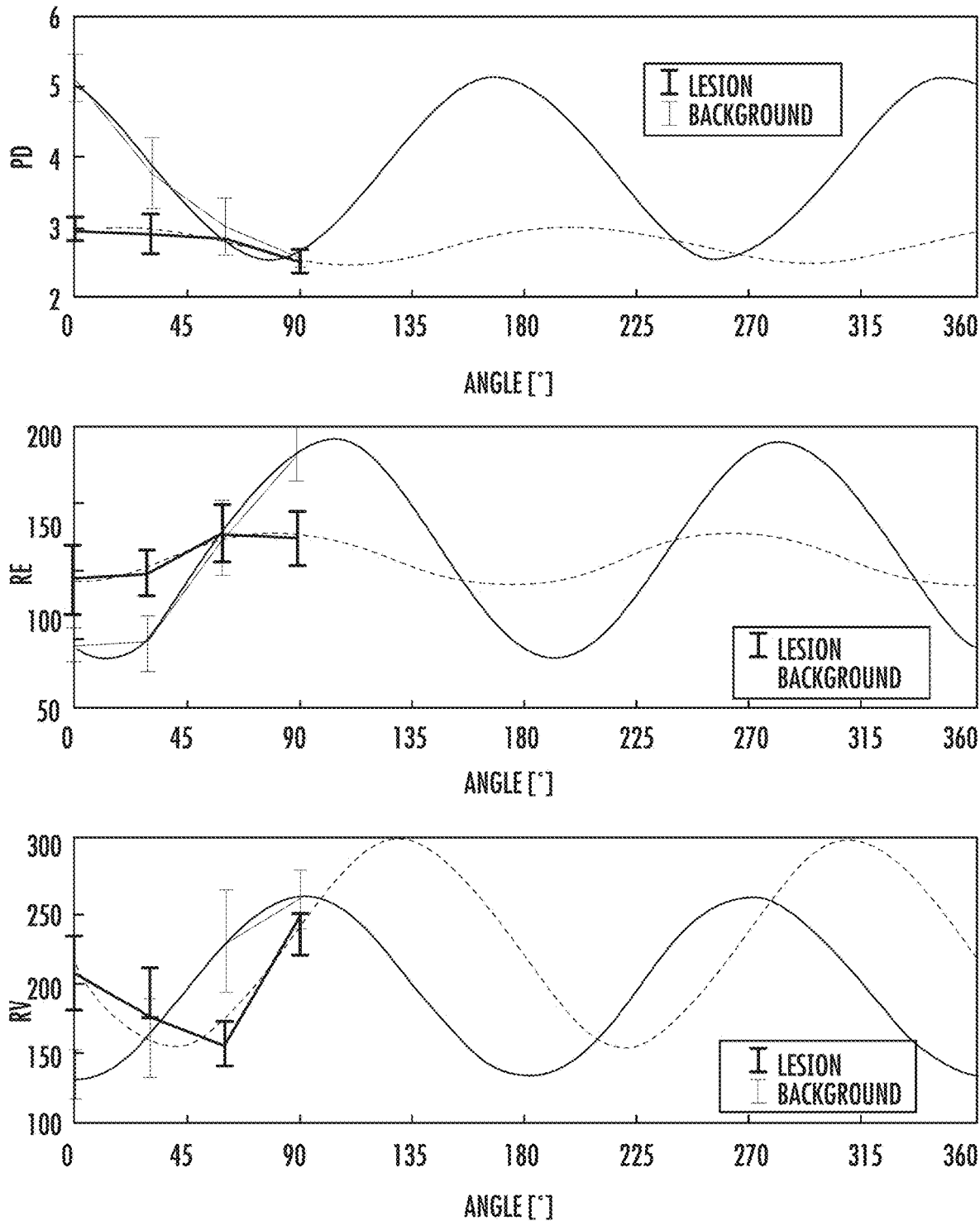
FIG. 6 shows the sinusoidal fits of Viscoelastic Response (VisR) Physical Displacement (PD), RE, and RV versus angle according to some embodiments of the present disclosure, for a patient with invasive ductal carcinoma.

FIG. 6 shows the sinusoidal fits of VisR PD, RE, and RV versus angle, for a patient with invasive ductal carcinoma. For this patient, the lesion had different DoA for PD, RE, and RV as compared to the background.

Figure 7:
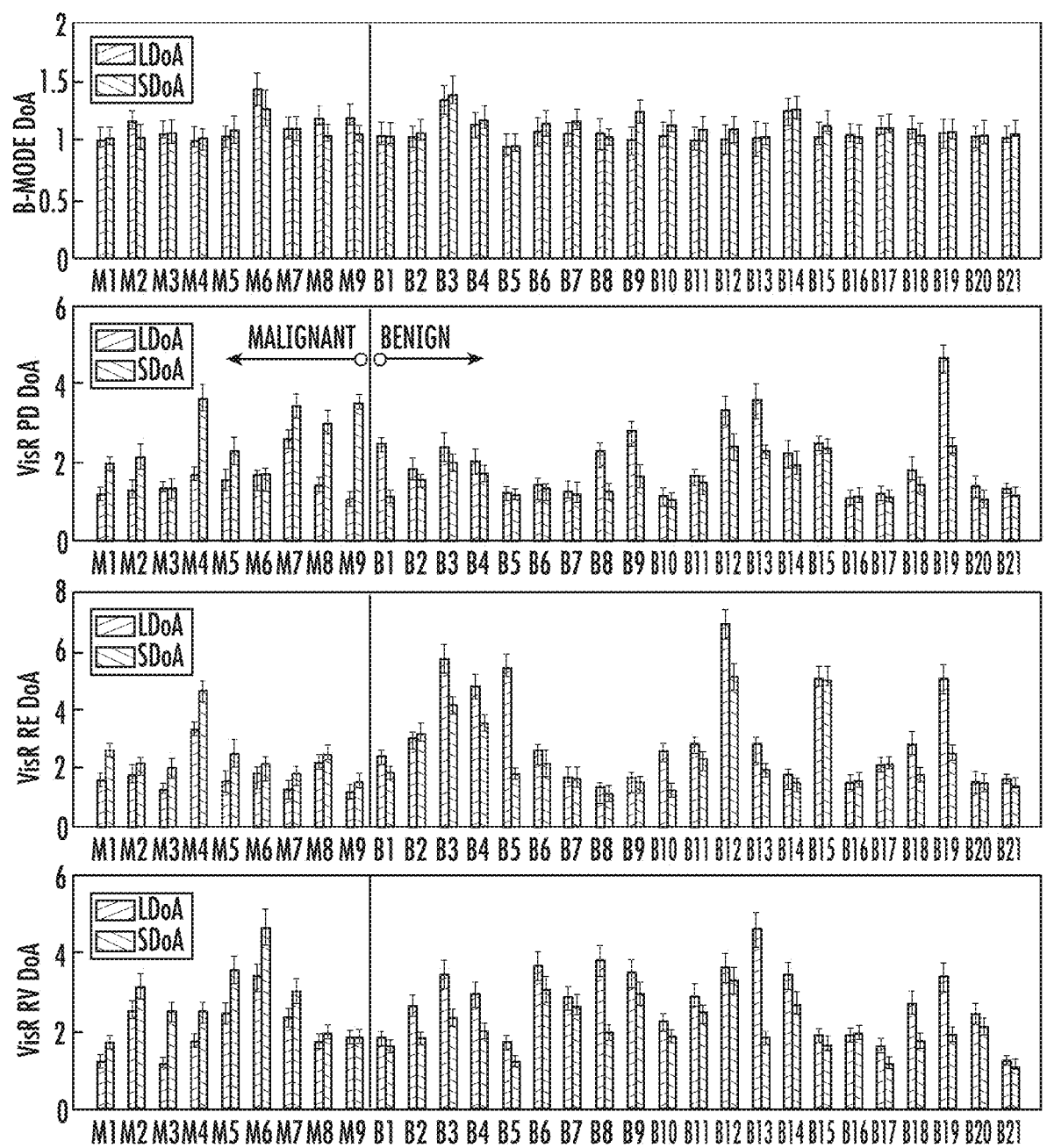
FIG. 7 illustrates degree of anisotropy values (DoA) for both lesion (LDoA) and surrounding tissue (SDoA) for B-Mode, VisR peak displacement, relative elasticity, and relative viscosity for all malignant and benign masses (N=30)

FIG. 7 illustrates the median LDoA (blue) and SDoA (yellow) values per mass for all patients (N=30), from top row to bottom row, derived from B-Mode, VisR PD, RE, and RV. It can be observed that B-Mode results are on average 1, indicating isotropy in B-Mode property. Additionally, for all VisR derived parameters, in malignant cases LDoA is lower than SDoA, whereas in benign cases LDoA is higher than SDoA.

These results suggest that VisR-derived mechanical anisotropy assessment could be diagnostically relevant to discriminating malignant from benign breast lesions.

Conclusions

DoA by PD, RE, and RV were equal and/or greater in the background than in the lesion for all malignant cases but consistently smaller in the background than in the lesion for all benign cases. To date, no other known ultrasound-based system is able to differentiate between malignant or benign breast cancer directly using images of anisotropy directly from the ratio of peak displacements, relative elasticity (RE), and relative viscosity (RV). Other technologies that are able to show parametric images dependent on the propagation of shear waves, which leads to decreased spatial and temporal resolution. Our method of creating anisotropy images for distinguishing malignant or benign breast cancer takes into consideration both lesion and surrounding tissue, and depends only on the maximal displacement at each position through depth, which makes the resolution of our technique finer than that of shear-wave based methods.

In the study described above, VisR ultrasound anisotropy was used to characterize differences in mechanical parameters between lesions and background tissue. In the following study, DoA, and more specifically, the ratio background to lesion DoA is used to characterize differences in mechanical parameters between lesions and background tissue.

Breast cancer screening allows identification of early stage cancer at a time before symptoms emerge, and allowing early treatment application with higher probability to result in a cure. However, high probabilities of false positives cause unnecessary medical expense and may downstream into adverse effects to patients. Achieving early breast cancer detection with high sensitivity and specificity still remains a challenge that may be met assessing additional tissue properties, in particular mechanical anisotropic properties by using acoustic radiation force. The objective of this study is to evaluate, in vivo, the diagnostic relevance of Viscoelastic Response (VisR)-derived metrics for mechanical anisotropy. We compare our in vivo human results against biopsy findings. This study analyzed 37 breast lesions imaged in vivo in women with BIRADS-4 or -5 ratings after standard screening. VisR relative elasticity (RE), relative viscosity (RV), and peak displacement (PD) were measured for each transducer orientation, and fit to a sinusoid by least-squares minimization, extrapolating to 360°. The ratio of the maximum to the minimum parameter value was calculated to reflect the degree of anisotropy (DoA). DoAs by PD, RE, and RV were statistically significantly greater in background than in lesion for all malignant cases but statistically significantly smaller in background than in lesion for all benign cases (Wilcoxon, p<0.05). These results suggest that VisR-derived mechanical anisotropy assessment could be diagnostically relevant for discriminating malignant from benign breast lesions.

I. Introduction

The main objective of breast cancer screening is to detect early-stage cancer, or precancerous lesions, at a time before symptoms emerge and when treatment is likely to be successful. Screening is beneficial when it averts progression of disease, but adverse effects to patients may result downstream from false positives. The current screening standard in the US is digital mammography, with sensitivity reported in the range of 0.40 to 0.85 [1], and a positive predictive value of 0.31 [2]. Sensitivity is improved by augmenting mammography with MRI and B-Mode ultrasound, but false positive rates also increase [3].

In addition to the previous clinical standards, studies have also shown that mechanical properties of breast tissue can be used for cancer detection, with both elasticity [4-7] and viscosity [8-10] demonstrated for discriminating malignant from benign lesions. Clinical studies have shown that the combination of B-Mode and compression elastography have higher performance (sensitivity: 0.87, specificity: 0.90), than B-Mode alone (sensitivity 0.80, specificity: 0.88) and compression elastography alone (sensitivity: 0.80, specificity: 0.81) [11-13]. These methods, however, are affected by the anisotropic behavior of breast tissue that is not captured when only performing a single 2D acquisition.

In particular to this study, tissue anisotropy in breast tumors has been shown to correlate with core biopsy result and tumor grade, with large cancers significantly more anisotropic than small cancers [14]. Previous studies have acquired strain and shear wave speed data at both radial and anti-radial locations relative to the lesion and shown correlation with malignancy [14-16]. However, a major shortcoming of these studies is the lack of alignment with the tissue's dominant direction of elasticity or viscosity, which may result in anisotropy measures that do not reflect the tissue's true degree of mechanical anisotropy. Further, while both MRI and ultrasound can be used to measure these biomarkers, ultrasound's cost effectiveness and ease of implementation render it an efficient platform to pursue.

Our research group has been developing a new ultrasound-based breast-screening tool to augment mammography, Viscoelastic Response (VisR) imaging. In our previous study [17] in 9 women with BIRADS-4 or -5 breast lesions, VisR-derived mechanical DoA was greater in the surrounding tissue background than in the lesion for all malignant cases but smaller in the background than in the lesion for all benign cases. These results suggested that lesion-to-background DoA assessment by VisR could be diagnostically relevant to discriminating malignant from benign breast lesions. In this study, we expand our assessment to 37 women and systematically evaluate the diagnostic relevance of VisR anisotropy-derived parameters.

II. Methods

A. Patient Selection

This study imaged 37 breast lesions (10 malignant, 27 benign) with BIRADS-4 or -5 ratings after standard screening imaging in vivo in women. Research subjects were recruited and imaging in the Breast Imaging Division of the University of North Carolina Hospitals, with IRB approval and signed consent.

After imaging, the evaluated lesions underwent clinically indicated biopsy with histological evaluation for identification of malignancy status. Exclusion criteria for this study included the following: 1) Incomplete data acquisition (N=3), 2) No presence of mass (N=2), 3) inconclusive histological evaluation (N=2). After exclusions, this study analyzed 30 breast lesions (9 malignant, 21 benign), from these cohort we also further assess lesions identified as fibroadenomas (N=9) vs carcinomas (N=9).

B. Viscoelastic Response (VisR) Imaging

Figures 8A, 8B:
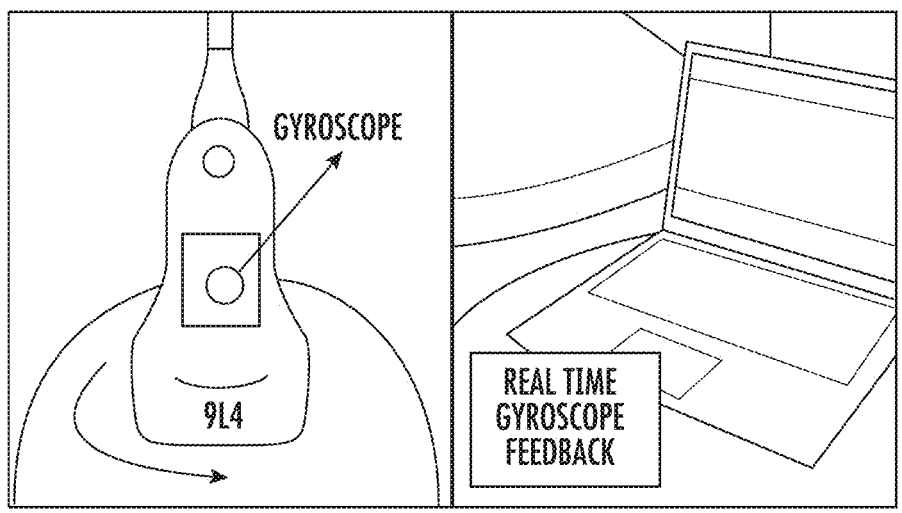
FIG. 8, pane (a), is a schematic diagram of an experimental setup including a 9L4 transducer attached to a gyroscope that is rotated from an initial 0° position to 30°, 60°, and 90° concentric locations. Pane (b) in FIG. 9 illustrates that real-time gyroscope feedback allows concentric rotation and positioning of the transducer.

Raw RF data were acquired using a Siemens S3000 Helix research system using a 9L4 transducer. To the transducer, a gyroscope was attached to guide manual rotation for data acquisitions at 0°, 30°, 60°, and 90° concentric orientations (see FIG. 1 and FIG. 8).

VisR ensembles consisted of two reference pulses, two acoustic radiation force (ARF) impulses, and 43 tracking lines. The two ARF impulses were each 300 cycles (~71 μs) in duration. The center frequency and focal configuration of the ARF impulses were 4.21 MHz and F/1.5, respectively. The impulses were separated by 8 tracking pulses (tARF=0.70 ms) and followed by 43 additional tracking pulses (3.74 ms). The tracking and reference pulses were conventional two-cycle A-lines at a center frequency of 6.15 MHz and pulse repetition frequency of 11.5 kHz. An F/1.5 focal configuration on transmit and dynamic focusing and aperture growth on receive were used for the reference and tracking pulses. VisR ensembles (reference+ARF+tracking pulses) were acquired in 40 lateral positions evenly spaced across a 2-cm lateral field of view for 2D imaging.

VisR displacements were measured using one dimensional axial cross-correlation (NCC) [18]. The obtained displacement profiles were then fit to the mass-spring-damper (MSD) model using a custom C++ implementation of the Nelder-Mead non-linear least-squares minimization [19-20]. VisR depth correction was applied to VisR relative elasticity and relative viscosity parameters, and VisR elasticity correction was applied to VisR relative viscosity results following the method in [21].

C. Anisotropy Assessment

Figure 9:
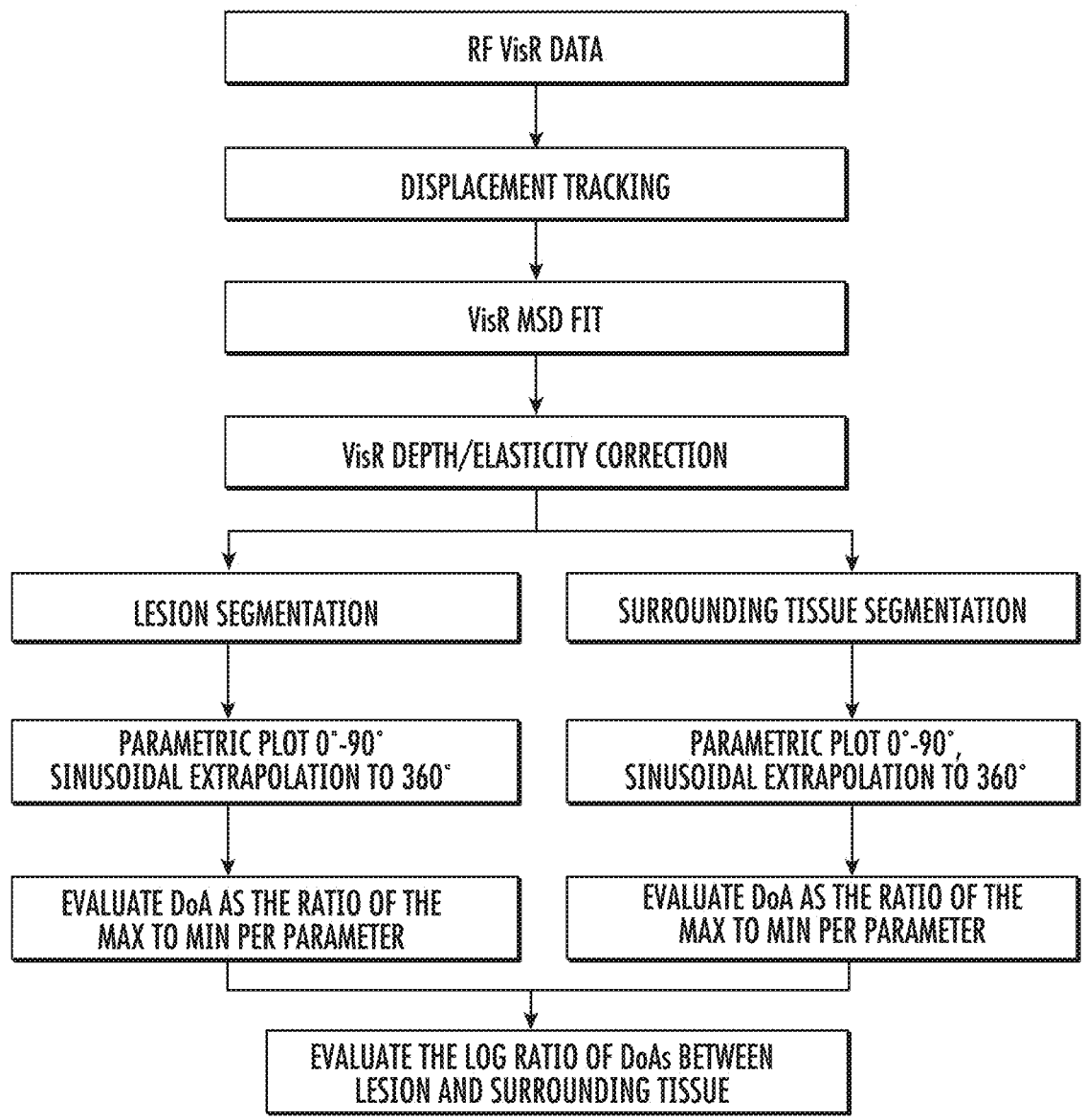
FIG. 9 is a flow chart of the parameter evaluation, starting with RF VisR data acquisition and finishing on the evaluation of log(LDoa/SDoA).

FIG. 9 includes a flow chart of the present methodology. B-Mode, VisR peak displacement (PD), relative elasticity (RE), and relative viscosity (RV) were measured in the lesion and also in the background surrounding tissue, for each transducer orientation. These values were assessed for malignancy differentiation through the median values from all acquisition angles (Wilcoxon-Ranksum test). Additionally, these parametric values were fit to a sinusoid by least-squares minimization, with extrapolation to 360°. Degree of anisotropy (DoA) was calculated as the ratio of the interpolated maximum to minimum parameter values. Finally, lesion DoA (LDoA), and surrounding tissue DoA (SDoA) were also assessed and combined as log(LDoA/SDoA) for each parameter and compared between malignant and benign masses.

Assessment was performed first using a statistical Wilcoxon-Ranksum test to identify significancy when differentiating benign vs. malignant masses. When combining LDoA and SDoA into log(LDoA/SDoA), a performance analysis was implemented to assess the sensitivity and specificity of malignancy detection using the Younden's index as the values that maximized the area under the curve (AUC) by calculating the receiver operating characteristic (ROC) curves, using the pathology outcomes as the validation standard.

III. Results

Figure 10A:
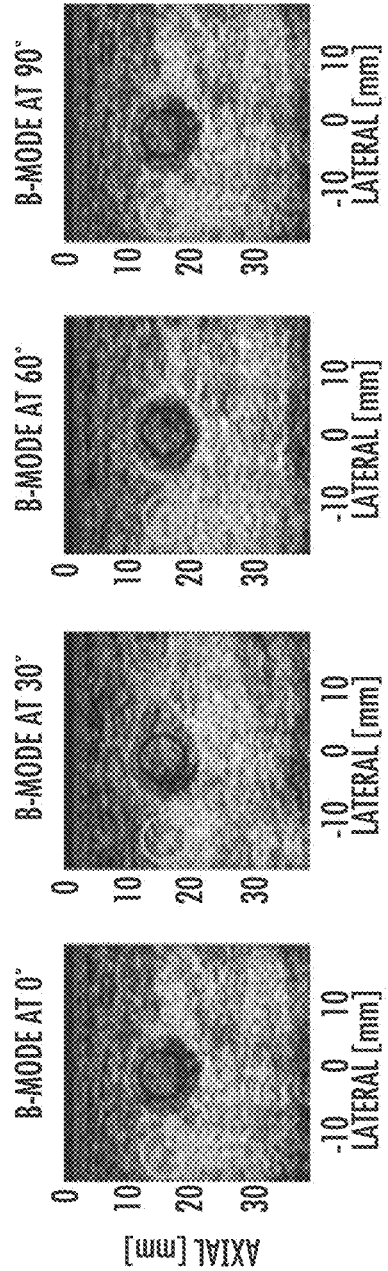
FIG. 10, pane (a), illustrates B-Mode images acquired at 0°, 30°, 60°, and 90° concentric rotations indicating mass (blue) and surrounding tissue (yellow). Pane (b) illustrates VisR peak displacement calculated on each location with a sinusoidal fit extrapolated to 360°.
Figure 10B:
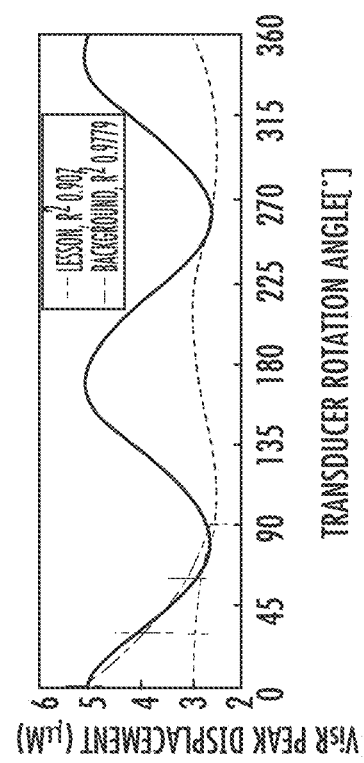

For a representative invasive ductal carcinoma from an 80-year-old female, B-Mode images are shown in FIG. 10, pane (a), acquired at 0°, 30°, 60°, and 90° concentric transducer rotations. Regions of interest are indicated for the lesion (blue) and its background surrounding tissue (yellow) for each position. VisR peak displacement values derived from the segmented regions are shown in FIG. 10, pane (b), where a sinusoid by least-squares minimization, with extrapolation to 360° is also shown in black for both regions. Table 1 depicts the median and standard deviation values calculated from all four concentric transducer rotations for all patients. P-values indicate that B-Mode and VisR PD, RE, and RV independent parametric amplitudes don't provide statistically significant differentiation between benign vs. malignant masses, and fibroadenomas vs. carcinomas.

Figure 11:
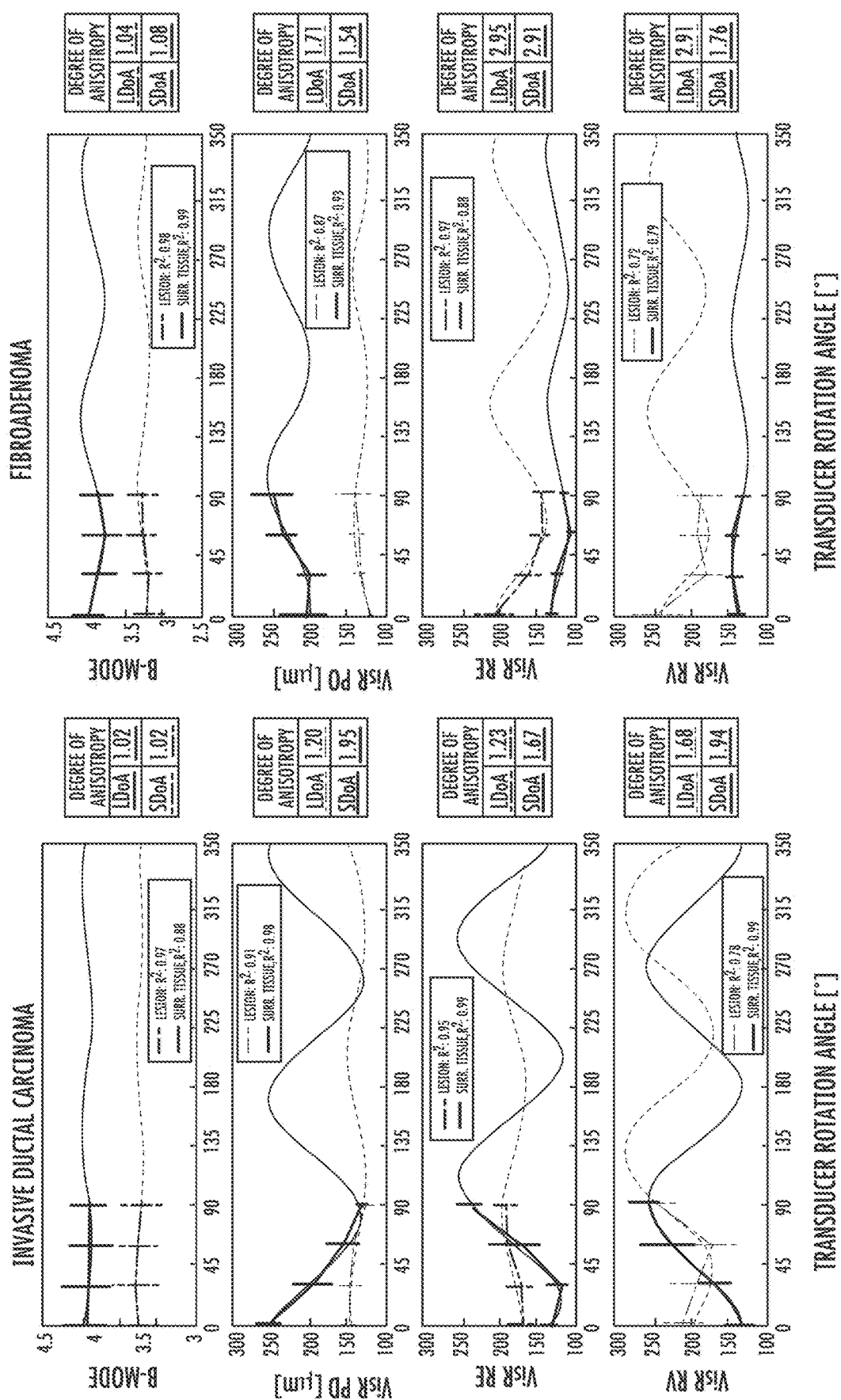
FIG. 11 illustrates example lesion and surrounding tissue parameters calculated for invasive ductal carcinoma (left) and fibroadenoma (right) BIRADS-5 masses. The lesion and surrounding tissue parameters are calculated from B-Mode, VisR peak displacement, relative elasticity, and relative viscosity. Degree of Anisotropy is calculated from both lesion and surrounding tissue as the ratio of the interpolated maximum to minimum parameter values.

FIG. 11 shows calculated parameter values for two breast mass examples from an 80-year-old female with an invasive ductal carcinoma, and a 50-year-old female with a fibroadenoma. From top row to bottom row, B-Mode, VisR PD, RE, and RV are calculated for the lesion and its surrounding tissue. DoA is also calculated per parameter for the lesion (LDoA) and its surrounding tissue (SDoA), as the ratio of the maximum to minimum parametric sinusoidal fitted values. DoAs calculated from the segmented regions in B-Mode indicated isotropic behavior for both carcinoma (LDoA=1.02, SDoA=1.02), and fibroadenoma (LDoA=1.04, SDoA=1.08). DoA values derived from all VisR parameters indicate anisotropic behavior in both lesion and surrounding media. For VisR PD, in the carcinoma the lesion has a lower DoA than the surrounding tissue (LDoA=1.20, SDoA=1.95), whereas in the fibroadenoma, the lesion has a higher DoA than the surrounding tissue (LDoA=1.71, SDoA=1.54). For VisR RE, in the carcinoma the lesion also has a lower DoA than the surrounding tissue (LDoA=1.23, SDoA=1.67), whereas in the fibroadenoma, the lesion has a higher DoA than the surrounding tissue (LDoA=2.96, SDoA=2.91). Finally for VisR RV, the previous trend repeats where in the carcinoma the lesion has a lower DoA than the surrounding tissue (LDoA=1.68, SDoA=1.94), whereas in the fibroadenoma, the lesion has a higher DoA than the surrounding tissue (LDoA=2.91, SDoA=1.76).

As described above, from the results illustrated in FIG. 7, it can be observed that B-Mode results are on average 1, indicating isotropy in B-Mode property, and, for all VisR derived parameters, in malignant cases LDoA is lower than SDoA, whereas in benign cases LDoA is higher than SDoA.

Figures 12A, 12B:
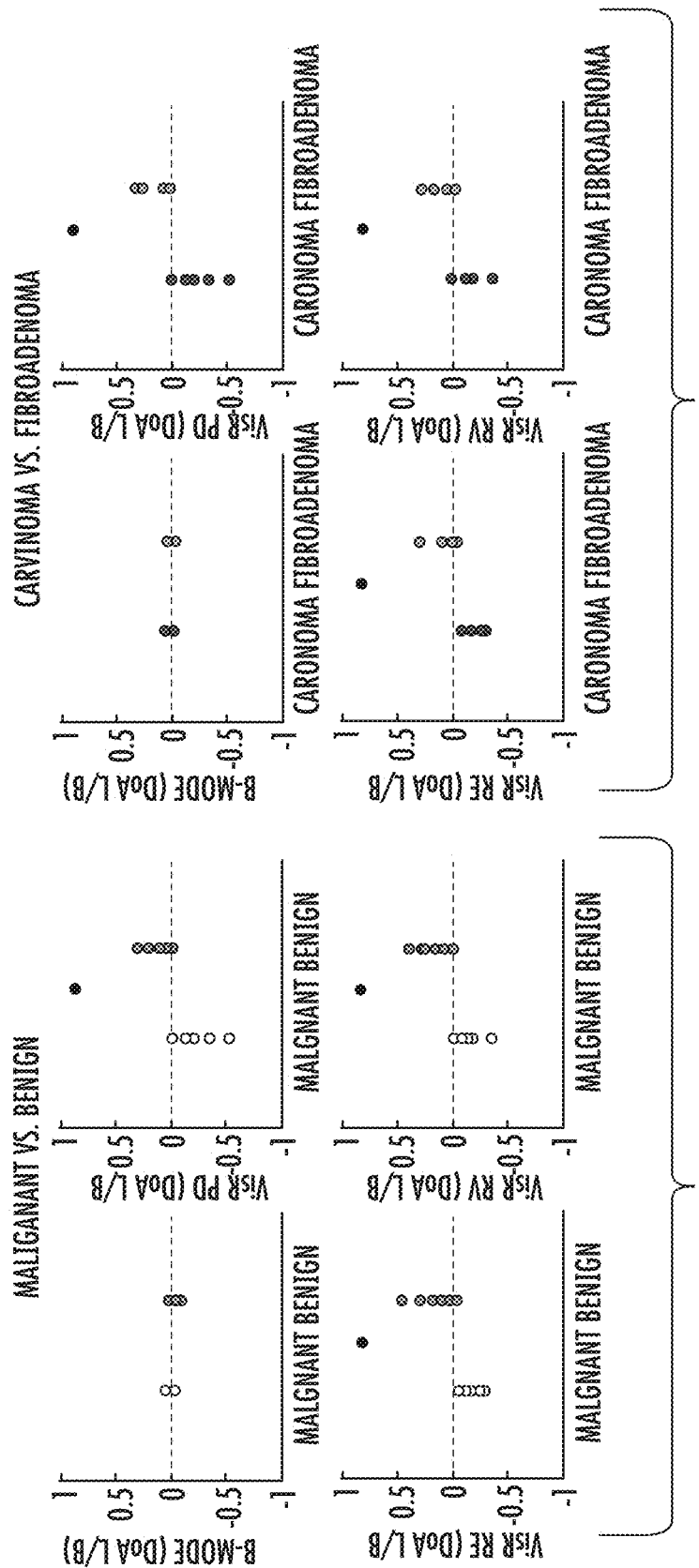
FIG. 12 illustrates (a) Malignant vs. benign mass comparison of log(LDoa/SDoA) calculated from B-Mode VisR peak displacement, relative elasticity, and relative viscosity. (b) Carcinoma vs. fibroadenoma mass comparison of log (LDoa/SDoA) calculated from B-Mode VisR peak displacement, relative elasticity, and relative viscosity.

FIG. 12 combines LDoA and SDoA in a logarithmic ratio to further merge mechanical anisotropy behaviors in both lesion and its surrounding tissue. FIG. 12, pane (a), illustrates malignant vs. benign values for B-Mode, VisR PD, RE, and RV-derived log(LDoA/SDoA), with statistical significance (Wilcoxon, p<0.01) achieved only for VisR PD, RE, and RV. FIG. 12, pane (b), illustrates carcinoma vs. fibroadenoma values for B-Mode, VisR PD, RE, and RV-derived log(LDoA/SDoA), with statistical significance (Wilcoxon, p<0.01) achieved also only for VisR PD, RE, and RV.

Figure 13A:
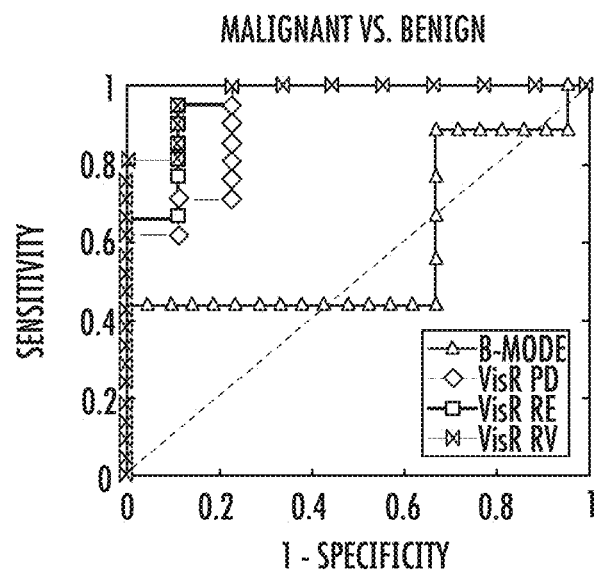
FIG. 13 illustrates ROC analysis of log(LDoa/SDoA) calculated from B-Mode VisR peak displacement, relative elasticity, and relative viscosity for differentiating (a) malignant vs. benign masses, and (b) carcinomas vs. fibroadenomas.
Figure 13B:
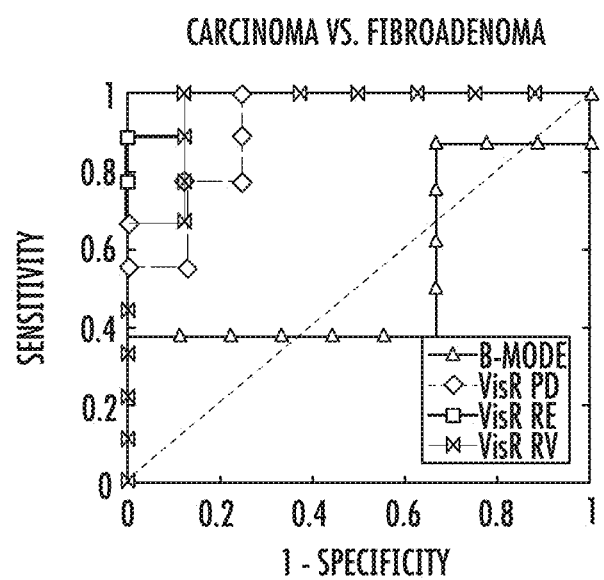

FIG. 13 depicts ROC curves for detecting, in pane (a), malignant vs. benign masses, and, in pane (b), carcinomas vs. fibroadenomas, with performance outcomes of AUC, sensitivity and specificity reported in Table 2. For differentiating malignant vs. benign masses, VisR RE and RV achieved the highest AUCs of 0.96 and 0.97, respectively, followed by VisR PD (0.93), and finally B-Mode (0.60). For differentiating carcinomas vs. fibroadenomas, VisR RE and RV achieved the highest AUCs of 0.98 and 0.96, respectively, followed by VisR PD (0.92), and B-Mode (0.54).

IV. Discussion

The in vivo breast lesion and surrounding tissue images shown in FIG. 10 quantitatively demonstrate that breast tissue presents a mechanically anisotropic behavior that can be characterized by the proposed method of concentric transducer rotations with a sinusoidal fit. Quantitative evaluations of parameter amplitudes without considering angle effects, shown in Table 1, and AUC analyses of sensitivity and specificity of log(LDoA/SDoA), shown in FIG. 13 and Table 2, further support the superior performance of the combination of lesion and surrounding tissue DoA relative to angle-independent B-Mode and VisR amplitudes.

Of interest is that using two regions of interest in tissue, i.e., lesion and its surrounding tissue, yielded higher performance than using the lesion region independently, where no statistically significant difference was found between malignant and benign masses. These results suggest that mechanical anisotropy both in the lesions and its surrounding tissue are complementary for identifying malignancy. The complementarity of the lesion and surrounding tissue behavior is consistent with prior MRI work showing that biological malignancy changes in structure and composition are not only present in the mass but also in the neighboring tissue.

Using VisR-derived log(LDoA/SDoA) ratios of PD, RE, and RV for parametric differentiation between malignant vs. benign masses generally perform comparably to each other via AUC analysis. In the case of comparing carcinomas vs. fibroadenomas, VisR-derived log(LDoA/SDoA) ratios maintain a similar performance, with AUC>0.91, sensitivity>0.88, and specificity >0.74. This suggests that elasticity and viscosity-derived anisotropy from lesion and surrounding tissue is relevant for identifying carcinomas in particular to fibroadenomas, but a bigger cohort study is needed to confirm this suggestion.

In addition to improving detection of malignant vs. benign breast masses, the present methodology offers the important advantage of characterizing anisotropic behavior. While previous studies characterized anisotropy by acquiring images at two perpendicular locations, being radial and anti-radial planes, or long/short axis, our methodology relies on four concentric data acquisitions guided by a gyroscope, followed by a sinusoidal fit extrapolated to 360. This approach allows identify the true degree of mechanical anisotropy, reducing bias from transducer positioning and tissue heterogeneities.

A limitation of this pilot study is the cohort size that disabled further data comparison between malignant and benign mass subtypes, and only enabled comparison between fibroadenomas and carcinomas. Future work involving larger data sets will consider benign subcategories such as necrosis, galactocele, and sclerosing adenosis, and malignant subcategories such as ductal carcinoma in situ and lobular carcinoma in situ, inflammatory, and triple negative breast cancer.

An additional factor influencing outcomes is the method of implementing the concentric acquisitions. While the sonographer was trained in breast ultrasound imaging, rotation of the transducer in a non-planar surface increased difficulty when maintaining a concentric rotation. Bias was reduced by using a real-time gyroscope feedback, but positioning error was still present. In the future, application of this technique using a 2D matrix array transducer for 3D volume acquisitions will minimize positioning bias.

V. Conclusions

This work demonstrates the potential of the VisR-derived degree of anisotropy to improve in vivo breast mass differentiation relative to conventional imaging. These results suggest that VisR-derived lesion-to-background mechanical anisotropy assessment is relevant to differentiating malignant from benign lesions in women with BIRADS-4 or -5 masses, in vivo.

The disclosure of each of the following references is hereby incorporated herein by reference in its entirety:

REFERENCES

[1] Cole E B, Zhang Z, Marques H S, et al. Assessing the stand-alone sensitivity of computer-aided detection with cancer cases from the digital mammographic imaging screening trial. Am J Roentgenol. 2012; 199(3):392-401.
[2] Kuzmiak C M. Breast Cancer Survivors: Does the Screening MRI Debate Continue? Acad Radiol. 2015; 22(11):1329-1330.
[3] Berg W A, Zhang Z, Lehrer D, et al. Detection of breast cancer with addition of annual screening ultrasound or a single screening MRI to mammography in women with elevated breast cancer risk. Jama. 2012; 307(13):1394-1404.
[4] Barr R G, Zhang Z. Shear-wave elastography of the breast: value of a quality measure and comparison with strain elastography. Radiology. 2015; 275(1):45-53.
[5] Grajo J R, Barr R G. Strain elastography for prediction of breast cancer tumor grades. J Ultrasound Med. 2014; 33(1):129-134.
[6] Youk J H, Gweon H M, Son E J. Shear-wave elastography in breast ultrasonography: the state of the art. Ultrasonography. 2017 October; 36(4):300.
[7] Giannotti E, Vinnicombe S, Thomson K, McLean D, Purdie C, Jordan L, Evans A. Shear-wave elastography and greyscale assessment of palpable probably benign masses: is biopsy always required?. The British Journal of Radiology. 2016 June; 89(1062):201.
[8] Qiu Y, Sridhar M, Tsou J K, Lindfors K K, Insana M F. Ultrasonic viscoelasticity imaging of nonpalpable breast tumors: preliminary results. Acad Radiol. 2008; 15(12):1526-1533.
[9] Nabavizadeh A, Bayat M, Kumar V, Gregory A, Webb J, Alizad A, Fatemi M. Viscoelastic biomarker for differentiation of benign and malignant breast lesion in ultra-low frequency range. Scientific reports. 2019 Apr. 5; 9(1):1-2.
[10] Zhang H, Guo Y, Zhou Y, Zhu H, Wu P, Wang K, Ruan L, Wan M, Insana M F. Fluidity and elasticity form a concise set of viscoelastic biomarkers for breast cancer diagnosis based on Kelvin-Voigt fractional derivative modeling. Biomechanics and Modeling in Mechanobiology. 2020 Apr. 25.
[11] Sood R, Rositch A F, Shakoor D, Ambinder E, Pool K L, Pollack E, Mollura D J, Mullen L A, Harvey S C. Ultrasound for breast cancer detection globally: A systematic review and meta-analysis. Journal of global oncology. 2019 August; 5:1-7.
[12] Zahran M H, E I-Shafei M M, Emara D M, Eshiba S M. Ultrasound elastography: how can it help in differentiating breast lesions?. The Egyptian Journal of Radiology and Nuclear Medicine. 2018 Mar. 1; 49(1):249-58.
[13] You Y, Song Y, Li S, Ma Z, Bo H. Quantitative and Qualitative Evaluation of Breast Cancer Prognosis: A Sonographic Elastography Study. Medical Science Monitor. 2019; 25:9272.
[14] Sinkus R, Tanter M, Catheline S, Lorenzen J, Kuhl C, Sondermann E, Fink M. Imaging anisotropic and viscous properties of breast tissue by magnetic resonance—elastography. Magnetic Resonance in Medicine. 2005 February; 53(2):372-87.
[15] Skerl K, Vinnicombe S, Thomson K, McLean D, Giannotti E, Evans A. Anisotropy of solid breast lesions in 2D shear wave elastography is an indicator of malignancy. Academic radiology. 2016 Jan. 1; 23(1):53-61.
[16] Chen Y L, Gao Y, Chang C, Wang F, Zeng W, Chen J J. Ultrasound shear wave elastography of breast lesions: correlation of anisotropy with clinical and histopathological findings. Cancer Imaging. 2018 Dec. 1; 18(1):11.
[17] Torres G, Moore C J, Goel L D, Steed D, Merhout J, Caughey M, Kirk S R, Hartman T S, Kuzmiak C M, Gallippi C M. Viscoelastic Response (VisR)-Derived Mechanical Anisotropy for Differentiating Malignant from Benign Breast Lesions in Women, in vivo. Proceedings of the IEEE IUS. 2019; 1372-1374.
[18] Pinton G F, Dahl J J, Trahey G E. Rapid tracking of small displacements with ultrasound. IEEE transactions on ultrasonics, ferroelectrics, and frequency control. 2006 Jun. 19; 53(6):1103-17.
[19] Selzo M R, Gallippi C M. Viscoelastic response (VisR) imaging for assessment of viscoelasticity in voigt materials. IEEE Trans Ultrason Ferroelectr Freq Control. 2013; 60:2488-2500.
[20] Selzo M R, Moore C J, Hossain M M, Palmeri M L, Gallippi C M. On the quantitative potential of viscoelastic response (VisR) ultrasound using the one-dimensional mass-spring-damper model. IEEE transactions on ultrasonics, ferroelectrics, and frequency control. 2016 Mar. 8; 63(9):1276-87.
[21] Hossain M M, Gallippi C M. Viscoelastic Response Ultrasound Derived Relative Elasticity and Relative Viscosity Reflect True Elasticity and Viscosity: In Silico and Experimental Demonstration. IEEE Transactions on Ultrasonics, Ferroelectrics, and Frequency Control. 2019 Dec. 30; 67(6):1102-17.

TABLES

TABLE 1

B-Mode, VisR peak displacement, relative elasticity, and relative viscosity amplitudes for both lesion and its surrounding tissue from (a) benign vs. malignant masses, and (b) fibroadenomas vs. carcinomas, p-value from Wilcoxon-Ranksum test.

|  | Benign (N = 21) | | Malignant (N = 9) | | p-value | Fibroadenoma (N = 9) | | Carcinoma (N = 9) | | p-value |
|---|---|---|---|---|---|---|---|---|---|---|
| B-Mode | 3.706 | (0.255) | 3.284 | (0.237) | 0.556 | 3.843 | (0.235) | 3.363 | (0.225) | 0.601 |
| VisR PD | 3.184 | (1.670) | 2.879 | (0.713) | 0.186 | 3.993 | (2.246) | 2.577 | (0.522) | 0.164 |
| VisR RE | 53.191 | (8.923) | 78.450 | (35.975) | 0.113 | 64.574 | (12.009) | 82.693 | (34.584) | 0.199 |
| VisR RV | 78.416 | (17.426) | 91.719 | (37.522) | 0.208 | 76.005 | (16.625) | 86.477 | (35.037) | 0.193 |

TABLE 2

Performance metrics of log(LDoA/SDoA) calculated from B-Mode,
VisR peak displacement, relative elasticity, and relative viscosity, comparing
malignant vs. benign masses, and carcinomas vs. fibroadenomas.

| | Malignant vs. Benign | | | | Carcinoma vs. Fibroadenoma | | |
|---|---|---|---|---|---|---|---|
| | B-Mode | VisR Peak Displacement | VisR Relative Elasticity | VisR Relative Viscosity | B-Mode | VisR Peak Displacement | VisR Relative Elasticity | VisR Relative Viscosity |
| AUC | 0.60 | 0.93 | 0.96 | 0.97 | 0.54 | 0.92 | 0.98 | 0.96 |
| Sensitivity | 0.33 | 1.00 | 0.95 | 0.95 | 0.33 | 1.00 | 0.89 | 1.00 |
| Specificity | 0.89 | 0.78 | 0.89 | 0.89 | 0.88 | 0.75 | 1.00 | 0.88 |

What is claimed is:

1. A method for evaluating mechanical anisotropy of a tissue sample to determine a characteristic of the tissue sample, the method comprising:

interrogating the tissue sample a plurality of times, each interrogation comprising:
applying a force having a direction, having a coronal plane normal to the direction of the force, and having an oval or other profile with long and short axes within the coronal plane, the long axis being oriented at a specified angle from a reference direction within the coronal plane; and
measuring displacement of the tissue sample resulting from application of the force, wherein the interrogations are taken at different angles of orientation within the coronal plane and different portions of the tissue sample are interrogated;

for each measurement, calculating one or more parameters for the respective angle of orientation, wherein the one or more parameters are one or more of a peak displacement, a relative elasticity, and a relative viscosity;

determining a first degree of anisotropy based on the one or more parameters calculated for each of the interrogations in a first portion of the different portions of the tissue sample, the first portion believed to contain a lesion;

determining a second degree of anisotropy based on the one or more parameters calculated for each of the interrogations in a second portion of the different portions of the tissue sample, the second portion believed to contain background tissue surrounding but not including the lesion;

determining that the first portion is malignant when the first degree of anisotropy is lower than the second degree of anisotropy; and determining that the first portion is benign when the first degree of anisotropy is higher than the second degree of anisotropy, wherein the tissue sample comprises a breast tissue sample.

2. The method of claim 1 wherein determining the first degree of anisotropy and second degree of anisotropy of the tissue sample to evaluate the characteristic of the tissue sample comprises:

fitting each of the calculated parameters to a sinusoid extrapolated to 360 degrees to create at least a first sinusoid representing the first portion of the different portions of the tissue sample and a second sinusoid representing the second portion of the different portions of the tissue sample; and for each sinusoid, determining the degree of anisotropy of the respective parameter based on a ratio of maximum to minimum values for that parameter.

3. The method of claim 1 wherein interrogating the tissue sample comprises interrogating the tissue sample using an ultrasound transducer.

4. The method of claim 2 wherein fitting each of the calculated parameters to a sinusoid comprises using a least squares minimization.

5. A system for evaluating mechanical anisotropy of a tissue sample to determine a characteristic of the tissue sample, the system comprising:

an ultrasound transducer;
one or more processors; and
memory storing instructions executable by the one or more processors for: controlling the ultrasound transducer to interrogate the tissue sample a plurality of times, each interrogation comprising:
controlling the ultrasound transducer to apply a force having a direction, having a coronal plane normal to the direction of the force, and having an oval or other profile with long and short axes within the coronal plane, the long axis being oriented at a specified angle from a reference direction within the coronal plane; and
measuring displacement of the tissue sample resulting from application of the force, wherein the interrogations are taken at different angles of orientation within the coronal plane and different portions of the tissue sample are interrogated;

the memory further storing instructions executable by the one or more processors for: for each measurement, calculating one or more parameters for the respective angle of orientation, wherein the one or more parameters are one or more of a peak displacement, a relative elasticity, and a relative viscosity;

determining a first degree of anisotropy based on the one or more parameters calculated for each of the interrogations in a first portion of the different portions of the tissue sample, the first portion believed to contain a lesion;

determining a second degree of anisotropy based on the one or more parameters calculated for each of the interrogations in a second portion of the different portions of the tissue sample, the second portion believed to contain background tissue surrounding but not including the lesion;

determining that the first portion is malignant when the first degree of anisotropy is lower than the second degree of anisotropy; and determining that the first portion is benign when the first degree of anisotropy is higher than the second degree of anisotropy, wherein the tissue sample comprises a breast tissue sample.

6. The system of claim 5 wherein determining the first degree of anisotropy and second degree of anisotropy based on the one or more parameters to evaluate a characteristic of the tissue sample includes:
fitting each of the calculated parameters to a sinusoid extrapolated to 360 degrees to create at least a first sinusoid representing the first portion of the tissue sample and a second sinusoid representing the second portion of the tissue sample;
for each sinusoid, determining the degree of anisotropy of the respective parameter based on a ratio of maximum to minimum values for that parameter; and for each parameter, phase aligning the sinusoid for that parameter for the first portion of the different portions of the tissue sample and the sinusoid for that parameter for the second of the different portions of the tissue sample.

7. The system of claim 6 wherein fitting each of the calculated parameters to a sinusoid comprises using a least squares minimization.

8. A non-transitory computer readable medium having stored thereon executable instructions that when executed by a processor of a computer control the computer to perform steps comprising:
controlling an ultrasound transducer to interrogate a tissue sample a plurality of times, each interrogation comprising:
applying a force having a direction, having a coronal plane normal to the direction of the force, and having an oval or other profile with long and short axes within the coronal plane, the long axis being oriented at a specified angle from a reference direction within the coronal plane; and
measuring displacement of the tissue sample resulting from application of the force, wherein the interrogations are taken at different angles of orientation within the coronal plane and different portions of the tissue sample are interrogated;
for each measurement, calculating one or more parameters for the respective angle of orientation, wherein the one or more parameters are one or more of a peak displacement, a relative elasticity, and a relative viscosity;
determining a first degree of anisotropy based on the one or more parameters calculated for each of the interrogations in a first portion of the different portions of the tissue sample, the first portion believed to contain a lesion;
determining a second degree of anisotropy based on the one or more parameters calculated for each of the interrogations in a second portion of the different portions of the tissue sample, the second portion believed to contain background tissue surrounding but not including the lesion;
determining that the first portion is malignant when the first degree of anisotropy is lower than the second degree of anisotropy; and
determining that the first portion is benign when the first degree of anisotropy is higher than the second degree of anisotropy, wherein the tissue sample comprises a breast tissue sample.

\* \* \* \* \*